United States Patent
Baxter et al.

(10) Patent No.: US 12,083,240 B2
(45) Date of Patent: Sep. 10, 2024

(54) 234 NM FAR UV C FILTER

(71) Applicant: LUMENLABS LLC, Poway, CA (US)

(72) Inventors: Kevin C. Baxter, Tulsa, OK (US); Wei Cao, Shanghai (CN); Min Shi, Shanghai (CN)

(73) Assignee: Lumenlabs LLC, Poway, CA (US)

( * ) Notice: Subject to any disclaimer, the term of this patent is extended or adjusted under 35 U.S.C. 154(b) by 0 days.

(21) Appl. No.: 17/327,499

(22) Filed: May 21, 2021

(65) Prior Publication Data

US 2022/0054683 A1 Feb. 24, 2022

Related U.S. Application Data

(63) Continuation-in-part of application No. 17/193,839, filed on Mar. 5, 2021, now Pat. No. 11,890,391.
(Continued)

(51) Int. Cl.
*A61L 2/24* (2006.01)
*A61L 2/10* (2006.01)
(Continued)

(52) U.S. Cl.
CPC ............... *A61L 2/24* (2013.01); *A61L 2/10* (2013.01); *F21V 7/06* (2013.01); *F21V 9/06* (2013.01);
(Continued)

(58) Field of Classification Search
CPC .......... A61L 2/24; A61L 2/10; A61L 2202/11; A61L 2202/14; G01C 3/00; G01J 1/42
See application file for complete search history.

(56) References Cited

U.S. PATENT DOCUMENTS 3,353,905 A 11/1967 Ellis
5,107,123 A 4/1992 Shi
(Continued)

FOREIGN PATENT DOCUMENTS

AU 2019100806 A4 8/2019
CN 206790749 U 12/2017
(Continued)

OTHER PUBLICATIONS

Buonannoa et al., Germicidal Efficacy and Mammalian Skin Safety of 222-nm UV Light; Aug. 10, 2017.

*Primary Examiner* — Sean E Conley
(74) *Attorney, Agent, or Firm* — Scott R. Zingerman; David G. Woodral; James F. Lea, III

(57) ABSTRACT

An excimer bulb assembly including an excimer bulb and a pass filter such that the excimer bulb assembly does not emit substantial UV radiation in wavelengths longer than 231 nm, 232 nm, 233 nm, 234 nm or 235 nm. The wavelengths are measured at an incident angle of zero (0) degrees to the filter plane. The pass filter is preferably constructed of a plurality of layers of hafnium oxide, and most preferably constructed of less than seventy five (75) layers of hafnium oxide. The excimer bulb, pass filter, and two electrical connectors may be adapted to form a cartridge which may be adapted to swivel along its main axis. The cartridge may further include a smart chip. The smart chip may retain and store information regarding the assembly and preferably retains hours of use of the excimer bulb.

15 Claims, 28 Drawing Sheets

Related U.S. Application Data which is a continuation of application No. 17/156,426, filed on Jan. 22, 2021, now Pat. No. 11,357,879, which is a continuation of application No. 17/080,390, filed on Oct. 26, 2020, now abandoned, application No. 17/327,499 is a continuation-in-part of application No. 17/160,230, filed on Jan. 27, 2021, now Pat. No. 11,752,228.

(60) Provisional application No. 63/183,937, filed on May 4, 2021, provisional application No. 63/069,436, filed on Aug. 24, 2020.

(51) Int. Cl.

| | | |
|---|---|---|
| *F21V 7/06* | (2006.01) | |
| *F21V 9/06* | (2018.01) | |
| *G01C 3/00* | (2006.01) | |
| *G01J 1/42* | (2006.01) | |
| *H01J 61/35* | (2006.01) | |
| *H01J 63/00* | (2006.01) | |
| *F21Y 115/10* | (2016.01) | |

(52) U.S. Cl.
CPC .............. *G01C 3/00* (2013.01); *G01J 1/42* (2013.01); *H01J 61/35* (2013.01); *H01J 63/00* (2013.01); *A61L 2202/11* (2013.01); *A61L 2202/14* (2013.01); *A61L 2202/25* (2013.01); *F21Y 2115/10* (2016.08)

(56) References Cited

U.S. PATENT DOCUMENTS

| | | | |
|---|---|---|---|
| 5,378,896 | A | 1/1995 | Knjaschewitsch et al. |
| 5,387,798 | A | 2/1995 | Funakoshi et al. |
| 6,398,970 | B1 | 6/2002 | Justel et al. |
| 6,437,346 | B1 | 8/2002 | Goudjil |
| 6,793,817 | B2 * | 9/2004 | Kuennen ............. H01J 61/20 |
| | | | 210/232 |
| 8,858,886 | B1 | 10/2014 | Chuah et al. |
| 9,214,783 | B2 | 12/2015 | Nomura et al. |
| 10,071,262 | B2 | 9/2018 | Randers-Pehrson et al. |
| 10,780,189 | B2 | 9/2020 | Randers-Pehrson et al. |
| 10,786,586 | B2 | 9/2020 | Igarashi |
| 10,864,287 | B2 | 12/2020 | Igarashi |
| 10,905,790 | B1 | 2/2021 | Moore et al. |
| 10,933,148 | B1 | 3/2021 | Patterson et al. |
| 10,960,094 | B1 | 3/2021 | Ismail |
| 11,007,292 | B1 | 5/2021 | Grenon et al. |
| 2002/0011434 | A1 | 1/2002 | Kuennen et al. |
| 2004/0021420 | A1 | 2/2004 | Tsuda et al. |
| 2004/0239900 | A1 | 12/2004 | Aoyama et al. |
| 2005/0000365 | A1 | 1/2005 | Nelsen et al. |
| 2005/0140292 | A1 | 6/2005 | Tiesler-Wittig |
| 2005/0143793 | A1 | 6/2005 | Korman et al. |
| 2006/0261291 | A1 | 11/2006 | Gardner, III |
| 2006/0289796 | A1 | 12/2006 | Havens et al. |
| 2007/0154823 | A1 | 7/2007 | Marson et al. |
| 2007/0255266 | A1 | 11/2007 | Cumbie et al. |
| 2008/0224068 | A1 | 9/2008 | Mii |
| 2009/0218512 | A1 | 9/2009 | Ranta et al. |
| 2010/0007492 | A1 | 1/2010 | Ressler et al. |
| 2010/0193707 | A1 | 8/2010 | Yamada et al. |
| 2010/0226029 | A1 | 9/2010 | Funasaka |
| 2012/0313014 | A1 | 12/2012 | Stibich et al. |
| 2012/0313532 | A1 | 12/2012 | Stibich et al. |
| 2013/0250395 | A1 | 9/2013 | Ichimura |
| 2014/0092238 | A1 | 4/2014 | Sandhu et al. |
| 2014/0116961 | A1 | 5/2014 | Bokermann et al. |
| 2015/0086420 | A1 | 3/2015 | Trapani |
| 2016/0095193 | A1 | 3/2016 | Mokhtari et al. |
| 2016/0195856 | A1 | 7/2016 | Spero |
| 2016/0230939 | A1 | 8/2016 | Van Hout |
| 2016/0317690 | A1 | 11/2016 | Dayton |
| 2017/0095583 | A1 | 4/2017 | Stamminger et al. |
| 2017/0112953 | A1 | 4/2017 | Dayton |
| 2017/0173195 | A1 | 6/2017 | Stibich et al. |
| 2017/0216466 | A1 | 8/2017 | Dujowich et al. |
| 2017/0281812 | A1 | 10/2017 | Dobrinsky et al. |
| 2017/0356602 | A1 | 12/2017 | Lin |
| 2018/0180226 | A1 | 6/2018 | Van Bommel et al. |
| 2018/0185533 | A1 | 7/2018 | Lalicki et al. |
| 2018/0264157 | A1 | 9/2018 | Benedek et al. |
| 2018/0296711 | A1 | 10/2018 | Brais et al. |
| 2019/0022260 | A1 | 1/2019 | Cole |
| 2019/0117802 | A1 | 4/2019 | Hishinuma et al. |
| 2019/0160305 | A1 | 5/2019 | Randers-Pehrson et al. |
| 2019/0171111 | A1 | 6/2019 | Kimsey-Lin |
| 2019/0176385 | A1 | 6/2019 | Hayakawa et al. |
| 2019/0192708 | A1 * | 6/2019 | Igarashi ............. G02B 5/208 |
| 2019/0255201 | A1 | 8/2019 | Rosen et al. |
| 2019/0328919 | A1 | 10/2019 | Saad et al. |
| 2019/0342942 | A1 | 11/2019 | Deros et al. |
| 2019/0360714 | A1 | 11/2019 | Konrad et al. |
| 2019/0381336 | A1 | 12/2019 | Randers-Pehrson et al. |
| 2019/0388706 | A1 | 12/2019 | Randers-Pehrson et al. |
| 2020/0085984 | A1 | 3/2020 | Randers-Pehrson et al. |
| 2020/0179544 | A1 | 6/2020 | Ufkes |
| 2020/0215214 | A1 | 7/2020 | Rosen et al. |
| 2020/0215215 | A1 | 7/2020 | Randers-Pehrson et al. |
| 2020/0234941 | A1 * | 7/2020 | Yagyu ................ A61L 2/10 |
| 2020/0267810 | A1 | 8/2020 | Chemel et al. |
| 2020/0282086 | A1 | 9/2020 | Silverman |
| 2020/0289686 | A1 | 9/2020 | Janik et al. |
| 2020/0335228 | A1 | 10/2020 | Yuan |
| 2020/0353112 | A1 | 11/2020 | Randers-Pehrson et al. |
| 2020/0397936 | A1 | 12/2020 | Deros et al. |
| 2021/0085810 | A1 | 3/2021 | Barron et al. |
| 2021/0158974 | A1 | 5/2021 | Seo et al. |
| 2021/0339183 | A1 | 11/2021 | Hourani et al. |
| 2021/0379215 | A1 | 12/2021 | Kelleher et al. |
| 2021/0386884 | A1 | 12/2021 | Brockschmidt, Jr. et al. |
| 2021/0398230 | A1 | 12/2021 | Gupta et al. |
| 2022/0016297 | A1 | 1/2022 | Huang et al. |
| 2022/0125963 | A1 | 4/2022 | Choi et al. |

FOREIGN PATENT DOCUMENTS

| | | |
|---|---|---|
| DE | 202020001197 U1 | 5/2000 |
| GB | 2531319 A | 4/2016 |
| GB | 2580838 A | 7/2020 |
| JP | 2010118267 A | 5/2010 |
| JP | 2012109389 A | 6/2012 |
| KR | 100849802 B1 | 7/2008 |
| KR | 1020160127469 A | 11/2016 |
| WO | 2008038548 A1 | 4/2008 |
| WO | 2010001441 A1 | 1/2010 |
| WO | 2014002591 A1 | 1/2014 |
| WO | 2015012592 A1 | 1/2015 |
| WO | 2019190967 A1 | 10/2019 |
| WO | 2020088803 A1 | 5/2020 |

* cited by examiner

234 NM FAR UV C FILTER

CROSS REFERENCE TO RELATED APPLICATION

This application claims the benefit of U.S. Provisional Application No. 63/183,937 filed May 4, 2021 entitled CARTRIDGE BASED UV C STERILIZATION SYSTEM and is a continuation-in-part of U.S. patent application Ser. No. 17/160,230 entitled HIGHLY EFFICIENT UVC BULB WITH MULTIFACETED FILTER filed on Jan. 27, 2021 and is a continuation-in-part of U.S. patent application Ser. No. 17/193,839 entitled CARTRIDGE BASED UV C STERILIZATION SYSTEM filed on Mar. 5, 2021 which is a continuation of U.S. patent application Ser. No. 17/156,426 entitled CARTRIDGE BASED UV C STERILIZATION SYSTEM filed on Jan. 22, 2021 which is a continuation of U.S. patent application Ser. No. 17/080,390 entitled CARTRIDGE BASED UV C STERILIZATION SYSTEM filed on Oct. 26, 2020 which claims the benefit of U.S. Provisional Application No. 63/069,436 entitled HUMAN SAFE UV C STERILIZATION SYSTEM filed Aug. 24, 2020, herein incorporated by reference in their entirety for all purposes.

FIELD OF THE INVENTION

The inventive system is in the field of Ultraviolet Light sterilization, specifically in the C band of wavelengths (UV-C). Such sterilization is presently used in hospital surgery rooms, burn wards, and similar areas that require a high degree of sterilization. The primary difference with these existing uses is the inventive system will be used safely in the presence of people and living tissues.

BACKGROUND OF THE INVENTION

UV-C is recognized as one of the most effective wavelengths at killing the small pathogens because the shorter the wavelength the more powerful it is. Only recently was it discovered that some of the wavelengths in this band are long enough to kill pathogens and short enough to not be able to penetrate living cells. Living cells are many times larger the tiny pathogens that we want to kill. UV-C is from 100 nm to 280 m, and the wavelengths that are generally being considered safe for exposure to human tissue are from 200 nm to 230 nm. UV-C does generate undesirable ozone, especially at wave lengths shorter than 200 nm.

Several studies have shown that hairless mice can be subjected to over 20 times the amount of 200 nm to 230 nm UV C as is presently suggested for humans, 8 hours a day, with no adverse effect. These studies have been performed in Japan at University and in the US at Columbia University. These studies are extending in time for up to 6 months, still with no adverse effects. Recently humans in Japan were also tested to 250 times the exposure of what is needed to kill 99.9% of pathogens and the test subjects showed no adverse effects, no sunburns, nothing.

There are several technologies that can generate UV light in the germicidal wavelengths, gas-discharge lamps have been around a long time and depending on the gases used can kill pathogens. Low pressure mercury generates 254 nm and has been the standard for decades, it is basically a fluorescent light without the phosphors on the inside that convert the UV to visible light. LEDs have recently been commercialized in the UV-A and UV-B spectrums, but they are very inefficient. There are a few in the longer wavelengths of the UV C spectrum. A research project in Japan recently made an LED that was in lower 200 nm's, the safer portion of the UV-C spectrum, but it was very inefficient and not practical for commercialization anytime soon.

Several companies are making UV-C excimer fixtures that emit 222 nm such as Ushio's 12W Care222, and another by Eden Park's Flat Excimer Lamps. The Ushio fixture has a flat faceplate filter that is separate from the bulb that blocks all unwanted spectrum that the bulb generates, and that spectrum is any wavelength longer than 230 nm when measured at the incident angle or 237 nm for off angle light that is very attenuated. The Eden Park device has no filter attached at this time and consequently emits 25% of its energy in the dangerous wavelengths from 230 nm to at least 380 nm. Luckily these bulbs are not very bright.

When these filters are not in place then these lights will emit spectrum that is not safe for living tissue. If a maintenance worker were to try and replace a bulb they could be exposed to harmful light. If the glass filter broke or degraded the user would be in danger.

Lastly the materials used are critical. UV-C cannot penetrate plastics and many glasses, only quartz glass can be used without huge losses or downright failure to emit the UV-C light. Even nitrogen and moisture in the air will also absorb or block the UV-C if it is transmitted too far through the air.

What is needed is an affordable and efficient UV sterilization light that would be good at killing pathogens with no chance to harm, under any situation, humans that would be present.

SUMMARY OF THE INVENTION

The inventive device provides a human-safe UV-C sterilizing bulb that can be used in continuous public places. The bulb will be safe in all situations, efficient, affordable, and could monitor itself and report conditions.

The present disclosure describes an excimer bulb assembly including an excimer bulb and a pass filter such that the excimer bulb assembly does not emit substantial UV radiation in wavelengths longer than 231 nm, 232 nm, 233 nm, 234 nm or 235 nm. The wavelengths are measured at an incident angle of zero (0) degrees to the filter plane. The pass filter is preferably constructed of a plurality of layers of hafnium oxide, and most preferably constructed of less than seventy five (75) layers of hafnium oxide. The excimer bulb, pass filter, and two electrical connectors may be adapted to form a cartridge which may be adapted to swivel along its main axis. The cartridge may further include a smart chip. The smart chip may retain and store information regarding the assembly and preferably retains hours of use of the excimer bulb.

Studies at Columbia University show that pass filters tuned from 200 nm-230 nm, measured at an angle of 0 degrees incident angle (perfectly perpendicular to the filter plane), kills the pathogens and don't hurt human cells and this is shown in prior art devices. But studying the energy curve just below 230 nm shows a very low energy being emitted by the bulb for the next several nanometers. This would allow changing the cutoff filter in the inventive device to 231 nm, or 232 nm, or 234 nm, or 235 nm, or even further before harmful wavelengths have sufficient energy for the need to be filtered. The inventive device would use 207 nm or 222 nm excimer technology combined with an integral band pass filter that would preferably substantially block all spectrum with wavelengths longer than 234 nm.

This small change to the filtration adds 2.5 times more usable emitted energy than the 200-230 nm filters and very little emissions in the 230-233 nm range. The filter material could be deposited directly on the bulb's envelope, which would be made of quartz glass, and this would block all harmful light even when handled during installation or maintenance. There are several well understood spikes of dangerous wavelengths in both the 207 nm and 222 nm bulbs. Ideally the inventive dynamic 234 nm filter would avoid having useless filtering for areas of the bulb's spectrum with no energy and complete filtering in the dangerous portions. The dynamic filter would not need to filter above 234 mm because the 222 nm bulb does not emit harmful levels of light above 200 nm. This could reduce the number of required layers from the traditional 80 plus layers down to about 60 layers for a dynamically filtered design that also has higher overall transmission and a lower cost. Certainly the number of layers could drop to under 75 with very little optimizing.

The 207 nm version requires the gasses bromine (Br) and argon and krypton (Kr). The 222 nm version uses krypton (Kr) and chloride (Cl). The filter material would ideally be very pure hafnium oxide deposited 2~3 um building a cutoff filter 234-400 nm with a depth of approximately 0.0001. This type of excimer bulb ideally uses Dielectric Barrier Discharge (DBD) and this is where the two primary electrodes are on the outside of the quartz envelope and in order to get the gasses to excite requires very high voltages, in the thousands of volts. Consequently, the gasses inside of the envelope will not be in contact with any metals that could contaminate them. Some Ushio lights have one conductor inside the envelope, sort of a hybrid, short-arc/DBD bulb. The inventive device avoids the problems of dissimilar materials and envelope contamination, and multiple types of glass needed, like Ushio's, by keeping all of the electrodes on the outside of the envelope. This inventive bulb does need a higher arc voltage but that is a small challenge for all of the benefits that a quartz only envelope solution provides.

The integral band pass filter could be deposited on a separate piece of quartz that would be permanently attached to the bulb's envelope using UV compatible adhesive around the edges. The filter would be integral to the finished assembly. This would protect users from UV exposure under all conditions including bulb changing and maintenance.

The inventive safe DBD device would also have an integrated captured reflector on the backside of the bulb's envelope and an additional 2 integral mirrors, one on each side of the bulb, set at 45 degrees to the filter face in order to maximize the light out. Light passing through the filter is heavily attenuated if it passes through at any angle other than absolutely perpendicular to the filter's plane. Light passing through at even 10 degrees from perpendicular is attenuated by over 50%, depending on the filter's composition, and the greater the angle the greater the attenuation and absorption.

The reflector could be a separate material that would be permanently connected to the bulb's envelope using UV compatible adhesive around the edges. The shape of the bulb would ideally be a flattened quartz tubing where the two flattened sides are parallel to each other. This design would be the cheapest and easiest configuration and is scalable. Other desirable but less optimum bulb shapes could be a tube-based design that has a complex shape which would allow the reflector on the back side to be optimized for different beam angles and patterns. A flattened circular tube-based bulb would emit a Lambertian pattern if desired.

The inventive safe DBD bulb will be cartridge based as to be easy to replace with rigid exposed conductors. The lifetime of 222 nm excimer bulbs is generally about 8000 hours, after they lose 10% brightness it goes down quickly from there. The high voltages and drivers of excimer bulbs are unique and cannot be connected to other power sources so each different bulb power/size will need a unique connector to avoid connections between electrically incompatible parts and polarization would be desirable as well. The primary high voltage electrode would ideally be a conductive ink made of silver or similar conductive metals printed in a mesh pattern over the non-opaque or filter area. The second primary electrode would also be at o volts and use the conductive ink as this would reduce parts. Because of the high voltages used in excimer bulbs a safety cutoff switch should be included in the inventive fixture in the case of a maintenance worker opening the fixture to safely replace a bulb.

Such a safe bulb will also have a built-in smart chip that has non-resettable serial number, manufacture date, use date, temperature boundary, and a Hobbs meter or hour meter. The smart chip would ideally use encryption in order to not be hacked. The bulb's fixture will be in communication with the smart chip on the bulb, and the fixture will have Internet Of Things (IOT) connectivity. The bulb's fixture will monitor the bulb life and when it was first turned on and shut down the bulb, if it or is it running over temperature, if it is near to end of life.

This will protect the users in case the filters begin to degrade, or the light intensity is not up to specification. It can notify or be polled by maintenance software and request replacement. The IOT connection can be used to talk to remote sensors that measure the output at different locations around the fixture's environment, where people are exposed. Because this type of bulb does not emit much visible light the fixture should include a multicolored LED indicator so that users can quickly at a glance know that the fixture is working, or not working properly. The bulb would also have a break wire running through the body and external glass so that if the body or glass were ever broken the break wire would also break and cause a bulb shutdown.

Because the light output degrades over time and the inventive safe fixture has feedback as to the environment's light level the fixture could boost the output over time to have a constant output level. The fixture would ideally have a light sensor to determine light output. The output level could be estimated by time used and that table could be programmed into the fixture so that the fixture could be constantly increasing the output power for a near-constant lumen output, or at least a good estimation.

When emitting a light that kills germs and the public is exposed to it, absolute safety is the primary standard that has to be met, tested and verified. The safeguards built into this fixture should not be luxuries, but should be requirements to allow a UV-C light to be exposed to the public.

When entering an area that is protected by the inventive device, the public should have access to the assembled data. They might ask, for example, "How long is the kill time for pathogens on surfaces, in the air? At what percentage output is the system running at? How much time can a human spend in this environment per day?"

The nature of DBD excimer bulbs is that the gasses can overheat and that causes the lighting level and lifetime to diminish so proper cooling is a requirement. The inventive safe bulb could have a ceramic or metallic heatsink on the back side. The envelope could also be extruded with linear fins to add surface area for convection cooling, similar to how an aluminum heat sink is designed. The fins would be on the outside of the light emitting envelope. A fan could blow air on the bulb in order to lower the gas temperature, especially when the power level is raised. A temperature sensor could part of the bulb to give temperature feedback and the fan's speed could be regulated as to have a constant envelope temperature.

Another reality of excimer bulbs is that they sometimes are hard to start in cold conditions and they need coiled filaments, resistors, or similar heating elements to preheat the gasses. These could be used to preheat the safe UV-C bulb at cold or even at normal start-ups and could be either inside or ideally outside the quartz envelope or encased in the ceramic heatsink. The power supply in the fixture would have to have additional circuitry to enable this feature. The inventive fixture would use pulse square wave rather than sine wave to drive the bulbs. Sine wave power for these high voltage applications are the standard but all of the energy below the peak voltage of the sine wave does not convert to light, it only makes heat.

The inventive safe device can use either 222 nm or 207 nm chemistries or both. Using two separate envelopes would allow tailoring the specific wavelength to best kill an emerging pathogen. Each chemistry has different drive voltages and arc gaps, but a power supply could easily be configured to drive either or both simultaneously. Ideally the inventive device will use DBD where the electrodes are on the outside of the glass envelope. This type of discharge requires very high voltages to get the gasses inside to excite but using this technique the gasses inside the envelope are never contaminated by electrode erosion, a common problem in gas discharge lamps when used over time. It would be desirable to combine the 222 nm and 207 nm gasses in a single bulb for greater efficiencies. The bromide and chlorine are in the same chemical family and could add to each other's strengths.

The inventive safe bulb would be used in environments where there is regular visible light coming from light fixtures and the inventive bulb could be combined with traditional light sources in a single fixture. If there was any adverse visible color emitting from the UV-C portion of the fixture the visible light's spectrum could be modified and mixed in such a way as to normalize the mixture or average of color coming from the fixture. This type of fixture would ideally be a "can", the type of fixture that is installed in a round hole in a ceiling.

The inventive safe system could be packaged as a typical light bulb. The ballast or power supply could be fitted in the base and the bulb would shine omnidirectionally, just like an LED or compact fluorescent light bulb, and it could have conventional lighting included as well.

The foregoing has outlined in broad terms the more important features of the invention disclosed herein so that the detailed description that follows may be more clearly understood, and so that the contribution of the instant inventors to the art may be better appreciated. The instant invention is not limited in its application to the details of the construction and to the arrangements of the components set forth in the following description or illustrated in the drawings. Rather the invention is capable of other embodiments and of being practiced and carried out in various other ways not specifically enumerated herein. Additionally, the disclosure that follows is intended to apply to all alternatives, modifications and equivalents as may be included within the spirit and the scope of the invention as defined by the appended claims. Further, it should be understood that the phraseology and terminology employed herein are for the purpose of description and should not be regarded as limiting, unless the specification specifically so limits the invention.

DESCRIPTION OF THE PREFERRED EMBODIMENTS

The embodiments herein and the various features and advantageous details thereof are explained more fully with reference to the non-limiting embodiments that are illustrated in the accompanying drawings and detailed in the following description. Descriptions of well-known components and processes and manufacturing techniques are omitted so as to not unnecessarily obscure the embodiments herein. The examples used herein are intended merely to facilitate an understanding of ways in which the invention herein may be practiced and to further enable those of skill in the art to practice the embodiments herein. Accordingly, the examples should not be construed as limiting the scope of the claimed invention.

Before explaining the present invention in detail, it is important to understand that the invention is not limited in its application to the details of the construction illustrated and the steps described herein. The invention is capable of other embodiments and of being practiced or carried out in a variety of ways. It is to be understood that the phraseology and terminology employed herein is for the purpose of description and not of limitation.

Figure 1:
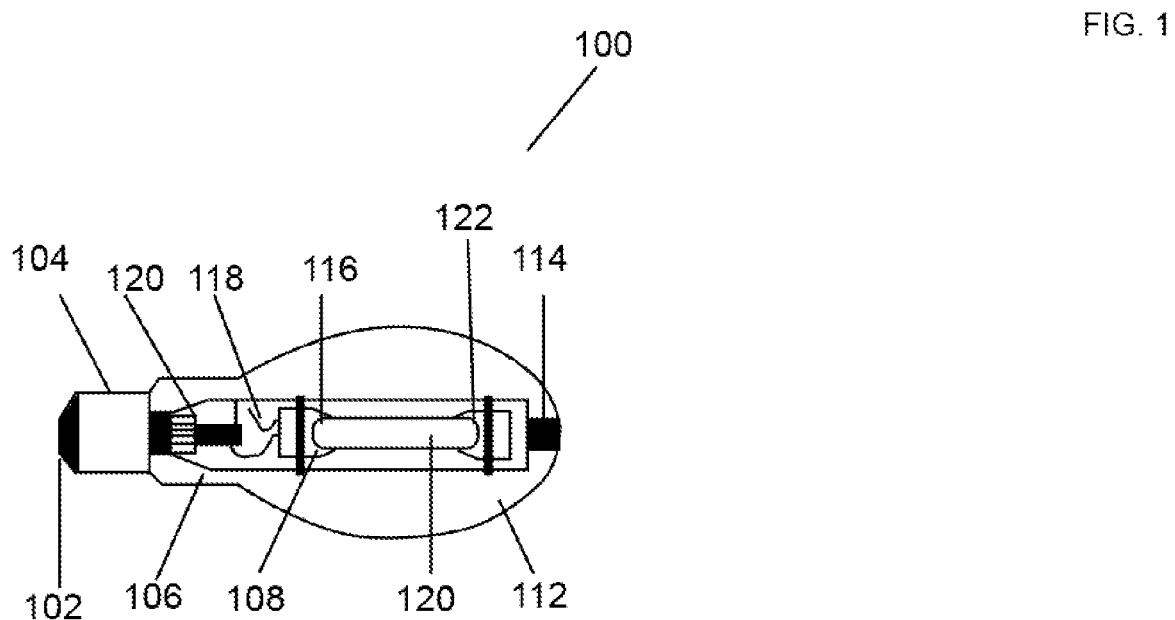
FIG. 1 Low pressure mercury bulb (prior art) line drawing from photo.

Referring now to the drawings, wherein like reference numerals indicate the same parts throughout the several views, a representative depiction of an (existing art) Low pressure mercury bulb 100 shown in FIG. 1. Where bulb 100 has several parts, the electrical contact points 102 and 104, the metal support structure 106, the primary electrode 108, the mercury and argon gas 110, the outer envelope 112, tip support 114, the striking electrode 116, a resistor 118, a glass base 120, and the second primary electrode 122.

Figure 2:
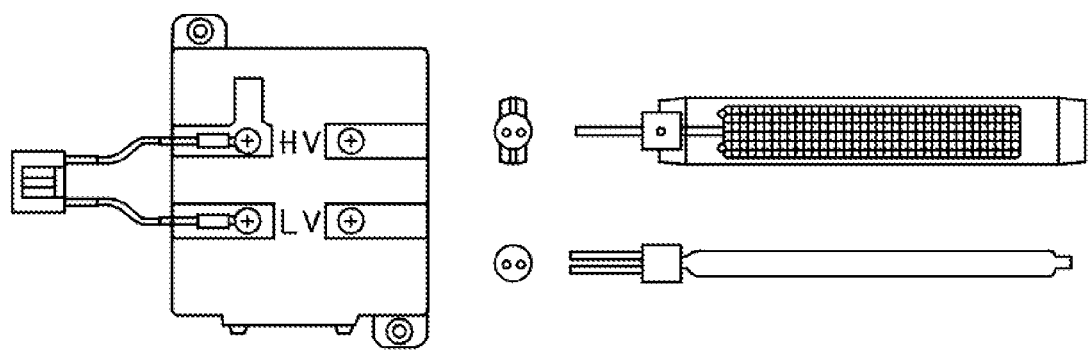
FIG. 2 Ushio Care222 excimer bulb and driver (prior art) line drawing from photo.

A newer and different technology is shown in FIG. 2 where an Ushio Care222 excimer bulb and driver system 200 is shown in block diagram form. The bulb 202 is driven by the driver 204 through 2 wires 206 and 208. The bulb has two primary electrodes 210 and 212. Housings and filters are separate and not shown.

Figure 3:
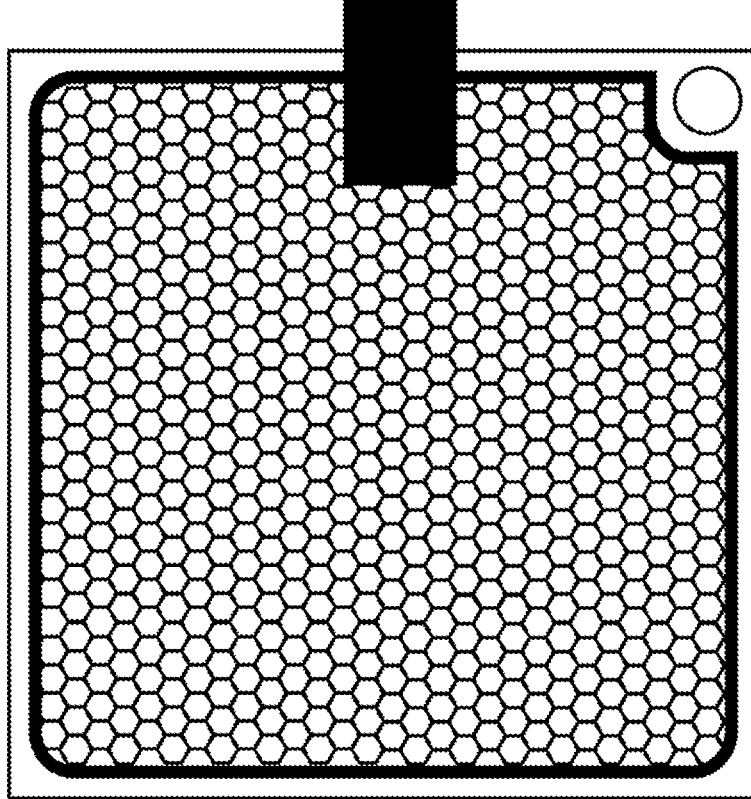
FIG. 3 Eden Park's Flat Excimer Lamp (prior art) line drawing from photo.

The next drawing in FIG. 3 shows a flat version of an excimer bulb that is Eden Park's Flat Excimer Lamp 300. It has two narrowly spaced flat sheets of quartz glass 302 and 304 with electrodes 306 and 308 on the outside of the front 310 and back 312 plates. The bulb has no filter or reflector.

Figure 4:
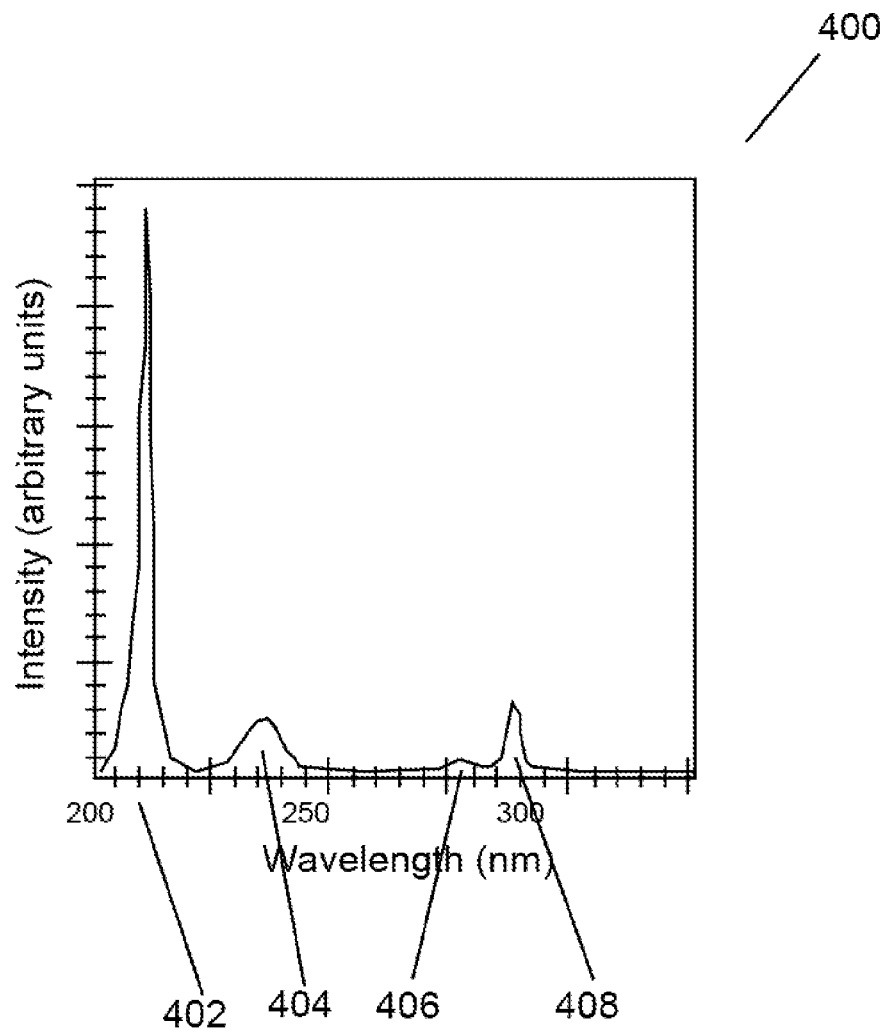
FIG. 4 Spectrum graph of a 207 nm Br Kr emission.

In FIG. 4 a spectral graph is shown of a 207 nm Br Kr emission 400. The primary emission spike 402 at 207 nm is a safe wavelength for human tissues and is deadly to small pathogens such as viruses and bacteria. Also shown is a small amount of emission at 230 nm 404 which is just at dangerous edge of spectrum incompatible with human exposure. Shown is additional emission at 270 nm 406 which even at this low level is extremely dangerous to human exposure. Lastly a spike of emission at 290 nm 408 and it is not safe for human exposure.

Figure 5:
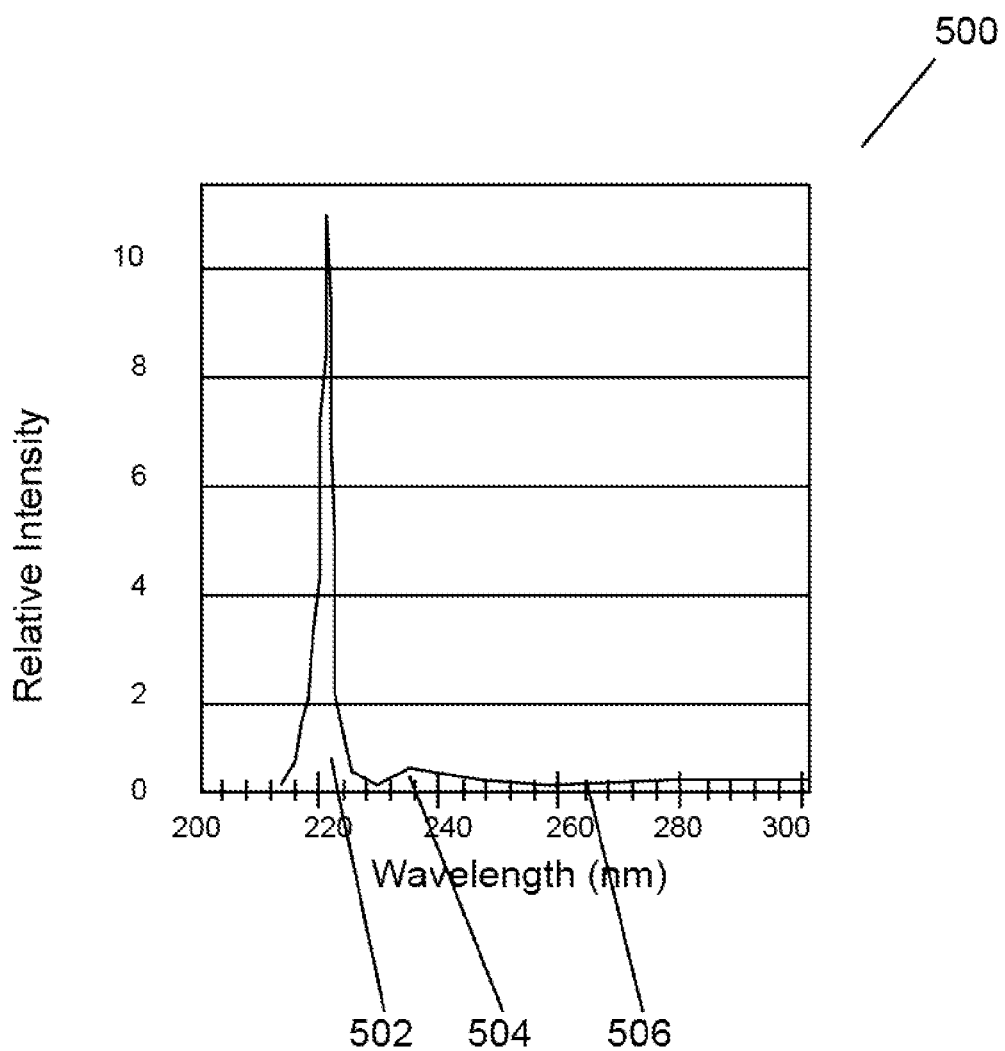
FIG. 5 Spectrum graph of a 222 nm Kr Cl emission.

In FIG. 5 there is a spectral graph of a different chemistry than what was shown before, this 222 nm Kr Cl emission 500. The primary emission spike 402 at 222 nm is a safe wavelength for human tissues and is deadly to small pathogens such as viruses and bacteria but energy curve 500 continues at a low level but rises into the deadly 238 nm 504 range. There is also a small bump of emission at the 258 nm range 506 and this is extremely dangerous even at such a low level. Note the flat low areas in between these peaks that would require virtually no filtering to be safe.

Figure 6:
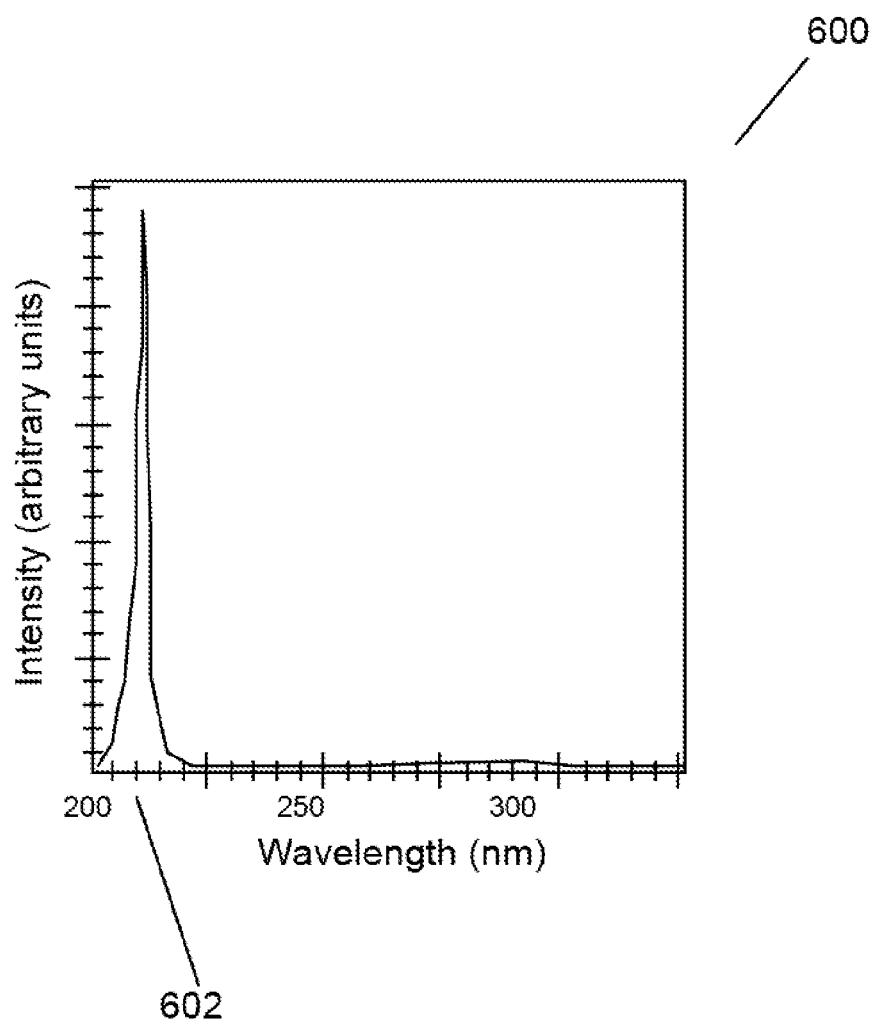
FIG. 6 Spectrum graph of a 207 nm Br Kr emission with proper filtration.

In FIG. 6 a spectral graph is shown of a safe 207 nm Br Kr emission 600 with a spike at 207 nm 602. 207 nm is a safe wavelength for human tissues and is deadly to small pathogens such as viruses and bacteria and due to subtractive filtering, there is no emissions in the dangerous wavelengths.

Figure 7:
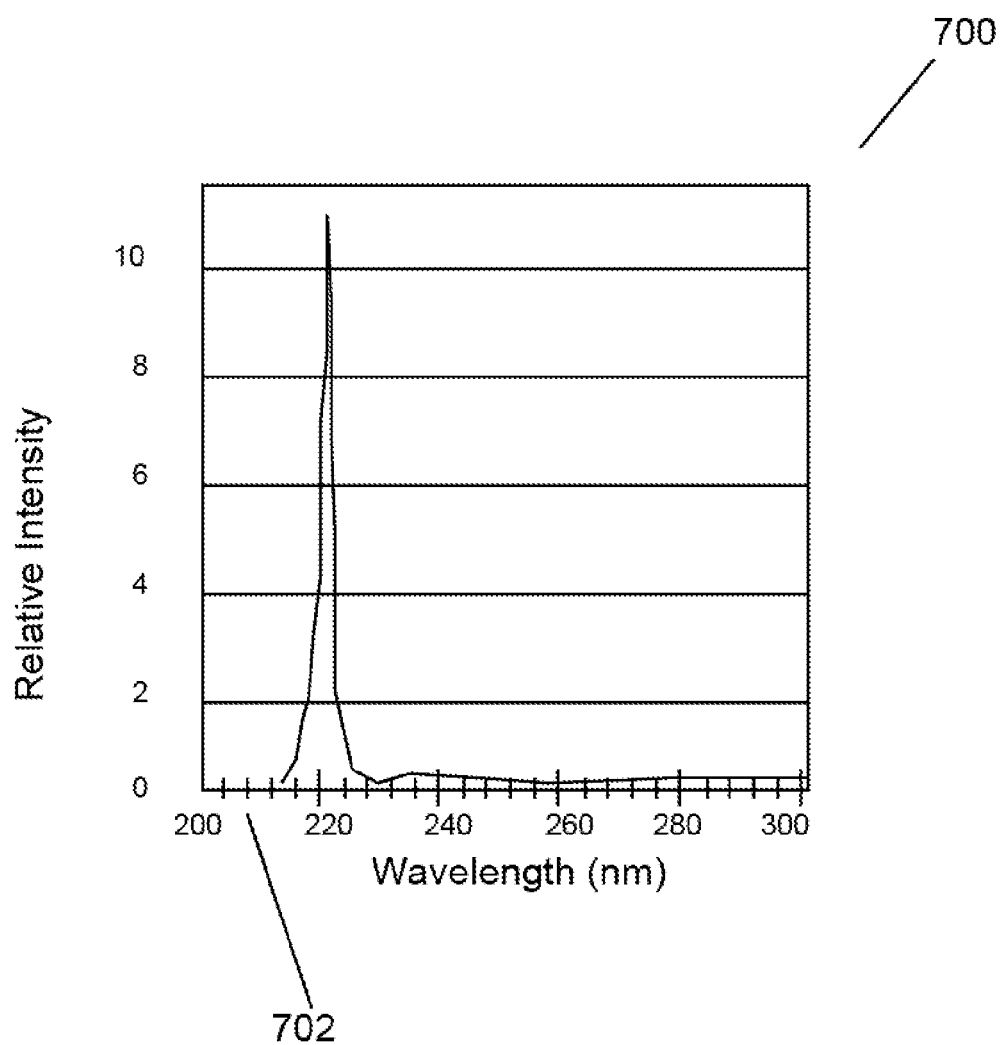
FIG. 7 Spectrum graph of a 222 nm Kr Cl emission with proper filtration.

In FIG. 7 a spectral graph is shown of a safe 222 nm Kr Cl emission 700 with a spike at 222 nm 702. It is believed that 222 nm is a safe wavelength for human tissues and is deadly to small pathogens such as viruses and bacteria and due to subtractive filtering, there is no emissions in the dangerous wavelengths.

Figure 8:
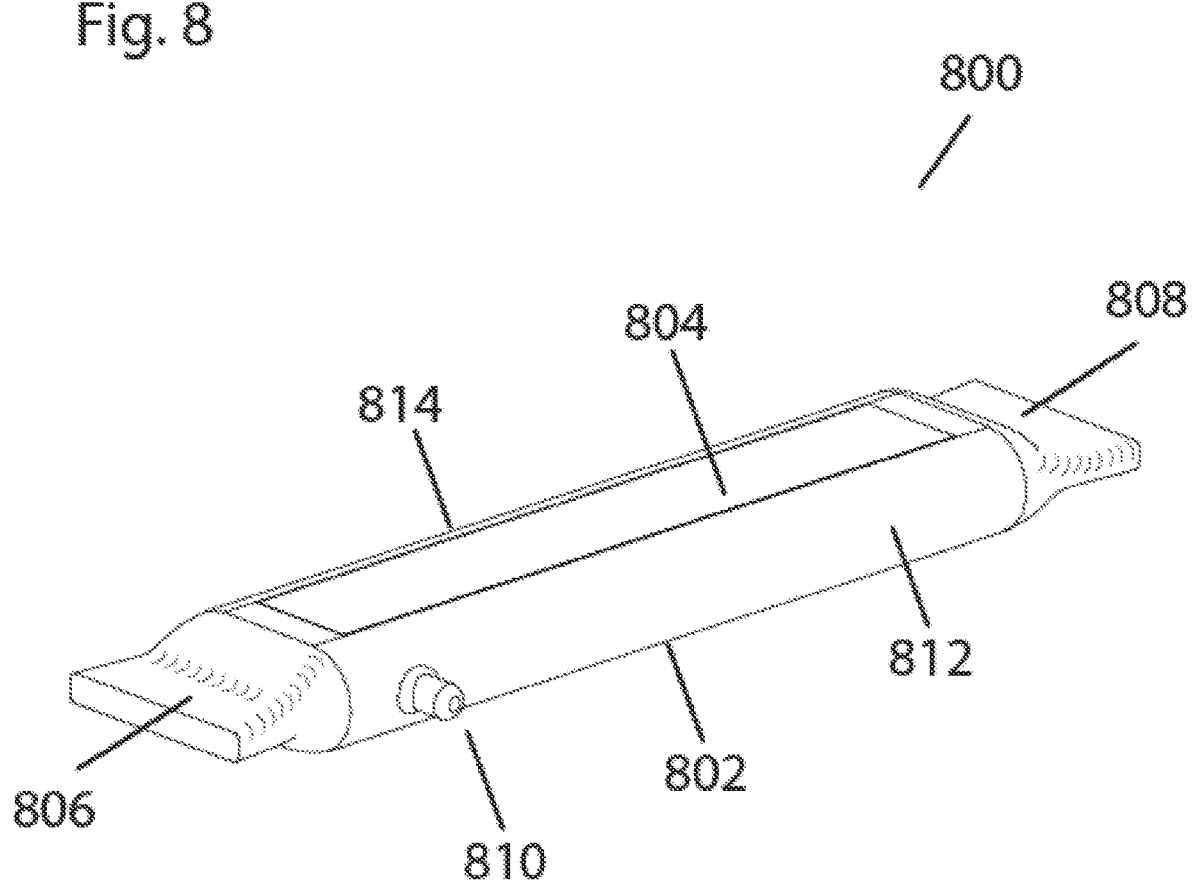
FIG. 8 Drawing of basic bulb.

In FIG. 8 an inventive excimer bulb 800 is shown. The bulb 800 has a quartz envelope 802 that contains a combination of gases at about 300 millibar pressure, depending on the specific chemistry involved, Br Kr at 207 nm or Kr Cl at 222 nm. The two flattened sides are parallel to each other and are approximately 10 mm apart, but this varies with different power levels, fill pressures, and drive voltages.

The quartz envelope 800 starts as a round cylinder and is heated and pulled through rollers that flatten the two sides, the front face 802, and the back face 804 to be parallel with each other. The ends of the flattened tube are then sealed at both ends 806 and 808 by heat welding to seal them. The fill point 810 as shown starts as a small fill tube that is melted shut after the bulb has been cleaned and filled with the low-pressure gasses. The sides of the bulb 812, and 814 allow light to pass as well, the right side 812 and the left side 814. These pathways of light have been ignored by prior art devices and enormous amount of wasted optical energy will be harnessed here by the inventive device.

Figure 9:
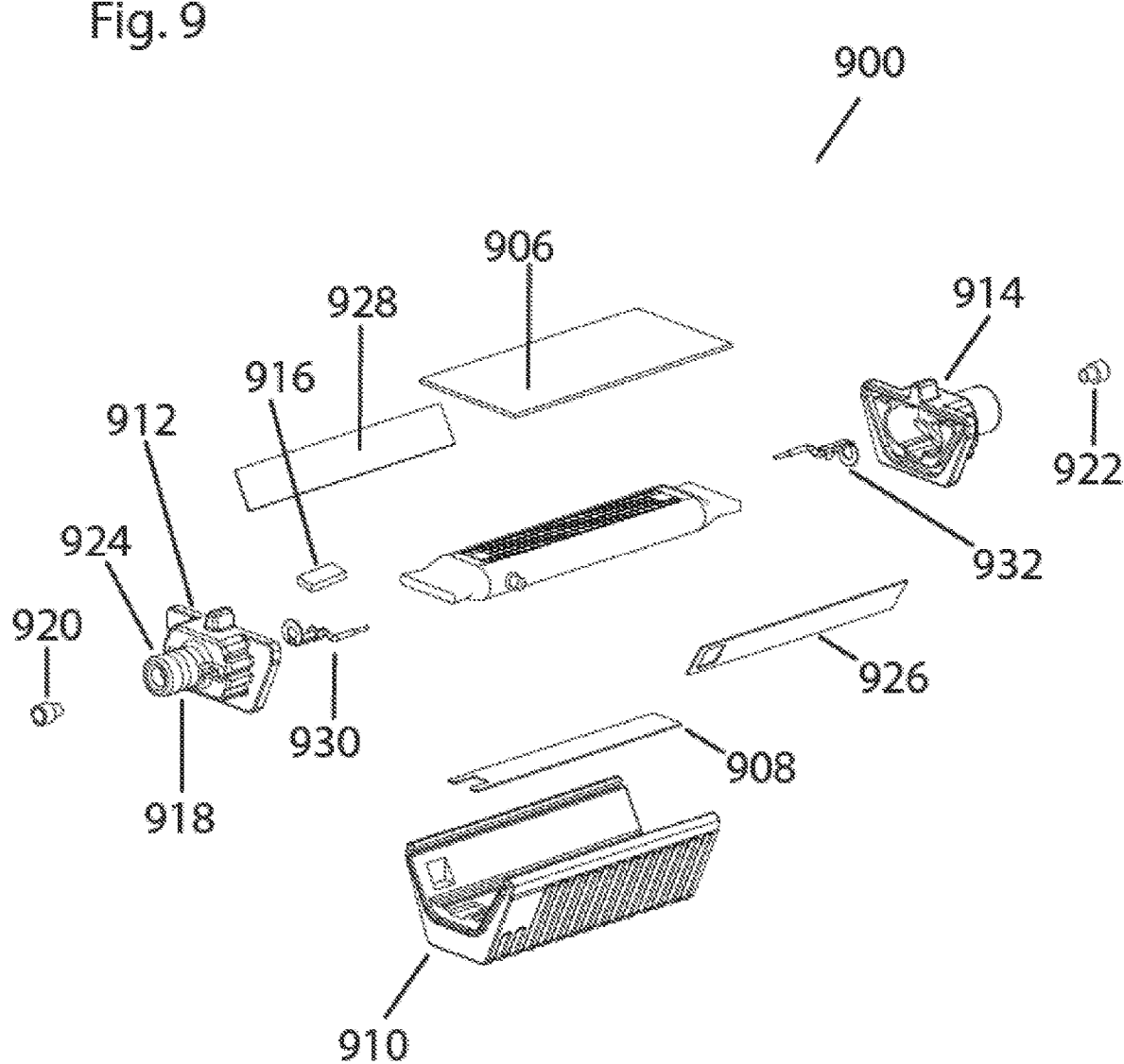
FIG. 9 Exploded isometric drawing of bulb assembly.

In FIG. 9 depicts an exploded view of a safe flattened tube design bulb assembly cartridge 900. Starting at the bulb 800 as the center of the assembly. The front electrode 902 is the ground, or 0 Volt, electrical grid and it is placed directly against the quartz bulb's face 802. It can be made of a non-corroding conductive metal such as molybdenum or silver. Ideally this front grid 902 or screen will be closest to the user and that is why the ground, or 0 Volt, potential was chosen for this side. To eliminate ozone production the grid would be applied as a conductive liquid or ink to eliminate oxygen from the electrical path. Similarly, the rear electrode 904 is the positive electrode. It too is placed directly against the quart envelope's back side 804. The voltage on this side is approximately 10,000 Volts and is placed away from the user as possible. This electrode 904 would be plated on or applied as a conductive ink to eliminate oxygen from getting between the conductive electrode and the path of high voltage electricity. The bulb could ideally be coated with evaporated quartz glass to protect the electrodes from oxygen. This is similar to the filter making process and would be very quick and inexpensive to implement.

A rear reflector 908 is generally flat but could be curved and is added against the outside of the rear electrode 904. The rear reflector 908 and the rear grid 904 could be combined as one part to both conduct electricity and reflect light, and as such could be a vapor plated on aluminum layer which would be deposited directly to the back side face 804 of the bulb 800 to further minimize parts and costs. Side reflectors 926, and 928 are set at 45% angles in order to capture light that escapes the sides 812 and 814 of the bulb 800 and send it directly forward and parallel to the light that is being emitted by the main face 804 of the bulb 800. Spaced as closely as possible to the two side reflectors 926 and 928 and the front electrode 902 is the UV filter plate 906 which is made of polished quartz and plated layers of Hafnium Oxide that form a narrow band pass filter in the 200 nm-234 nm range. Ideally these layers would be applied dynamically as to completely filter the harmful wavelengths and ignore the very low levels of UV C for a much more efficient filter, possibly only 60 layers and less than 80 layers.

A heatsink 910 which could be aluminum but ideally would be ceramic to add electrical insulation to the high voltage back electrode 904. The heatsink 910 will block any unfiltered light from emitting through cracks between the mirrors 908, 926, and 928 or out of the ends of the bulb 800. Ideally the heatsink 910 would also capture many of the individual elements of the bulb assembly mentioned so far including the bulb 800, the rear reflector 908, the side reflectors 926 and 928, the rear electrode 904, the front electrode 902, and the front filter plate 906 and it would be tightly sealed using UV compatible epoxy would be used around the edges of the bulb 812 to stabilize the mechanical connections between these components and completely seal air and dust incursion. Existing art designs allow for air to be blown directly over the bulbs and dust could then deposit over time to the bulbs and the inside face of the filter. Dust can absorb large amounts of the UV C light and become very inefficient very quickly. The inventive device eliminates these faces from dust incursion by making a sealed cartridge 900 using the end caps 912 and 914. These end caps 912 and 914 of the bulb assembly 900 will be made of ceramic and the end cap 912 would encapsulate thermal sensors and a smart chip 916, as well as provide a mechanical rotation point for the bulb including detents 918 for preset individual position stops in a fixture. This means a light emitting cartridge that has no wires or flying leads to connect. The smart chip and temperature sensor 916 has an hours of operation meter, serial number, manufacturing date, temperature, out of range flags, and encryption communication capabilities to prevent counterfeit operation. There as a conductive jumper 930 in connection with the front electrode 902 that passes through the ceramic end cap 912 and then is electrically connected by to a conductive pin 920. Similarly, there is a conductive jumper 932 that is in connection to the rear electrode 904 that passes through the ceramic end cap 914 and then is electrically connected to a conductive pin 922. There are 3 plated-on conductive traces 924 around the ceramic end cap 912 that are connected to the smart chip and thermo sensor 916. These traces 924 allow communication from the bulb cartridge 900 to contacts on the fixture receiver to allow the fixture to communicate with these chips 916. Such mechanical and electrical connections are well understood by one skilled in the art and other methods of connectivity could be used. This assembly becomes an easy to replace safe UV C bulb cartridge 900 that is hermetically sealed with all high voltage portions insulated and removed from those who handle it or are exposed to it.

Figure 10:
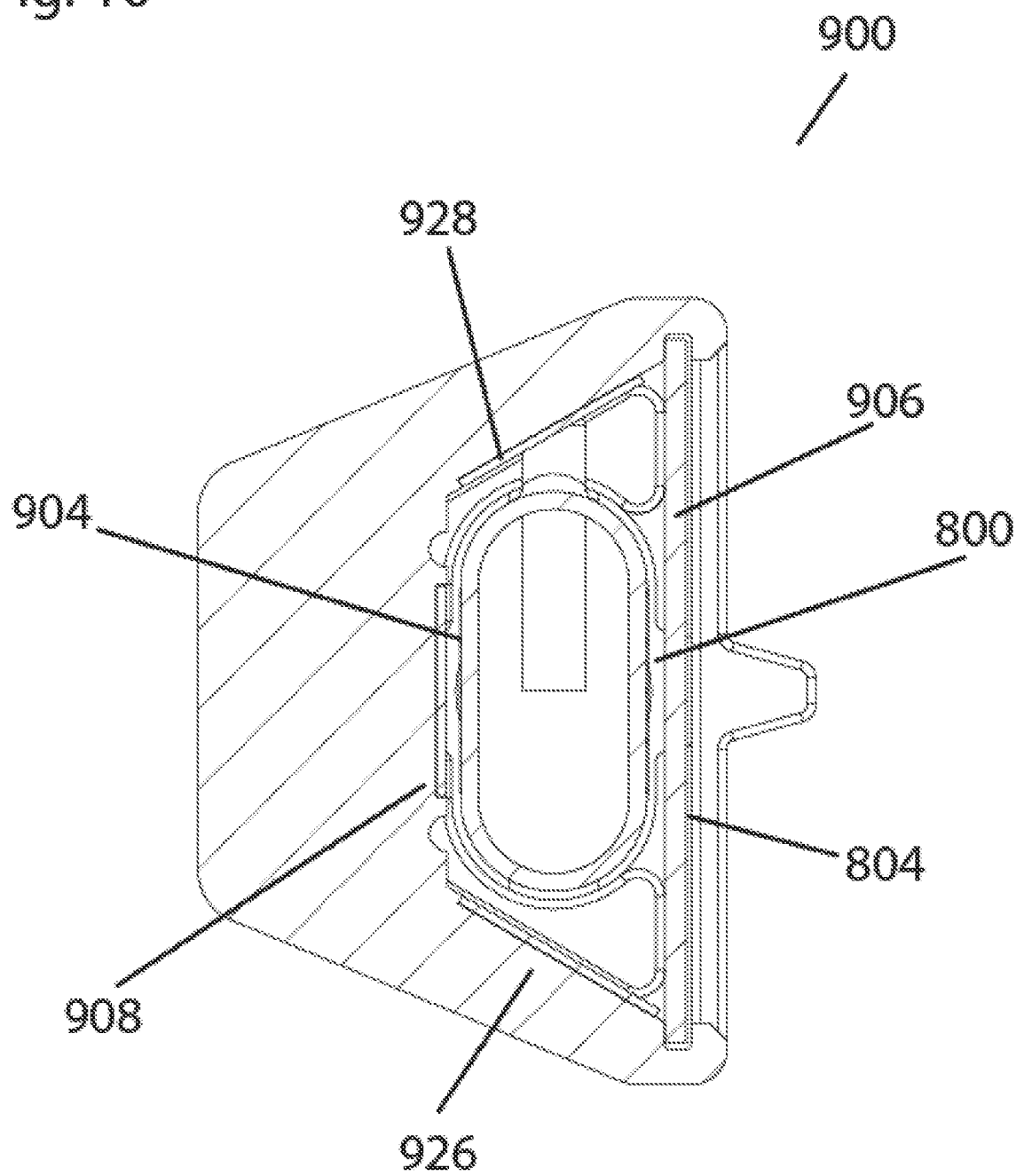
FIG. 10 Side view section of bulb assembly.

FIG. 10 depicts a sectioned side view of an assembled safe UV-C bulb cartridge 900. The bulb 800 has the negative electrode 904 plated or applied directly to the quartz. Similarly, the positive electrode 902 applied directly on the bulb's 800 front face 804. Behind the negative electrode 904 is the rear reflector 908. The right-side reflector 926 and the left side reflector 928 are angled at 45 degree angles to the front face 804. They are all captured and contained by the ceramic heatsink 910. There is a tiny air space between the bulb 800 and the filter 906 that is sealed by the ceramic pieces and ideally UV tolerant sealant.

Figure 11:
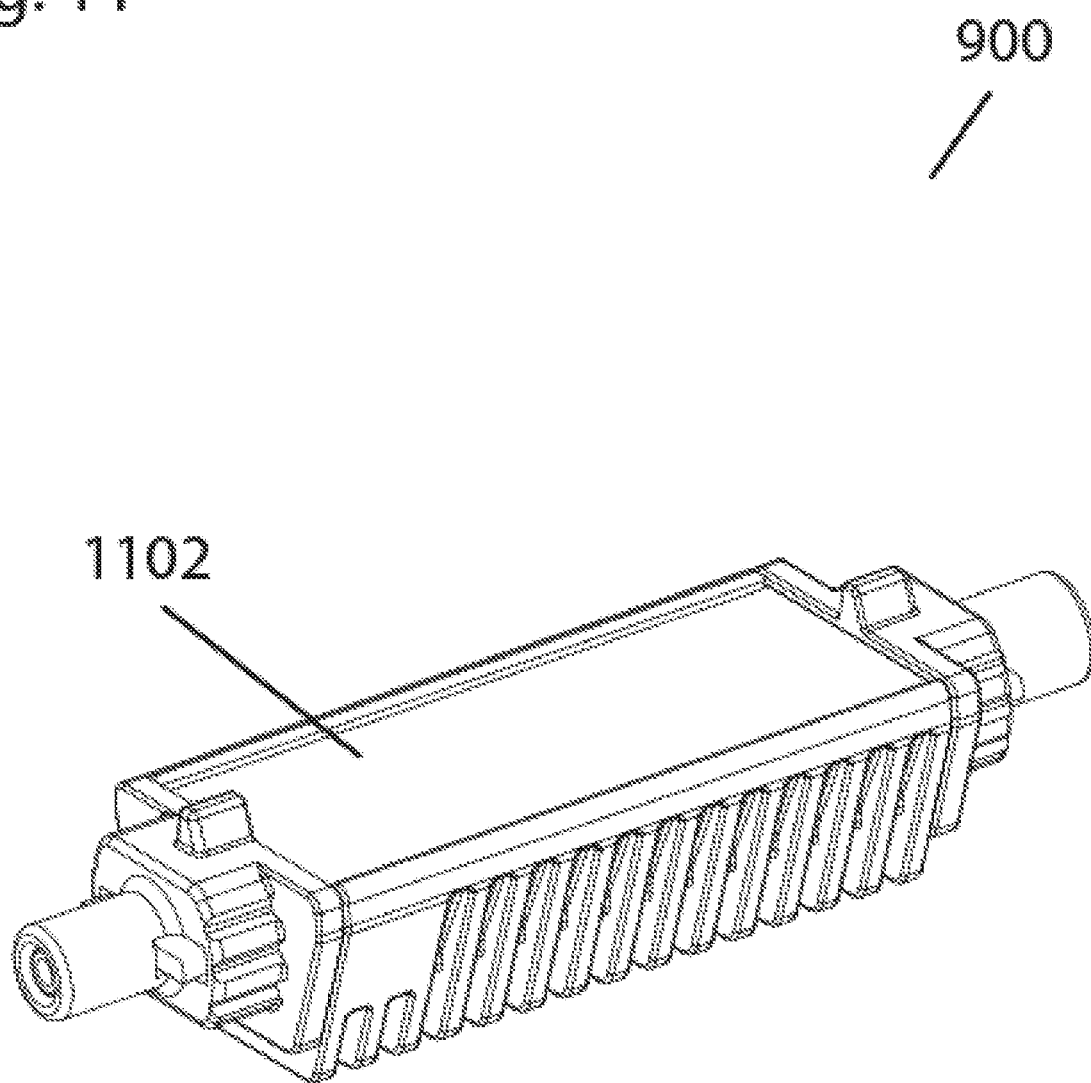
FIG. 11 Isometric view of bulb cartridge.

FIG. 11 depicts an assembled safe UV-C bulb cartridge 900. The assembled cartridge 900 has an optical aperture 1102 that is sealed around the edges such that air and dust and unfiltered light are eliminated from passing through.

Figure 12:
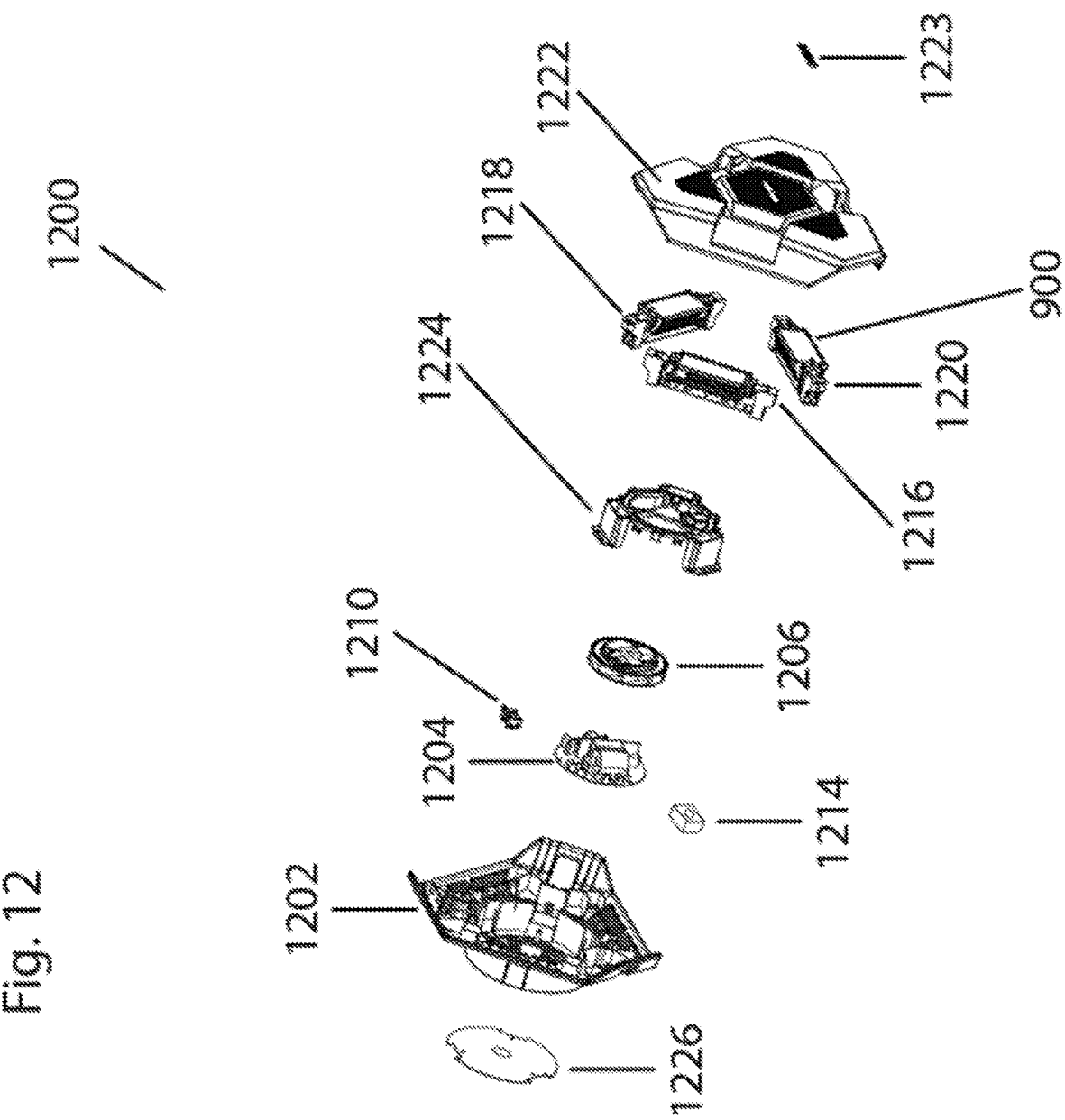
FIG. 12 Exploded view of multi-bulb fixture.

FIG. 12 shows an exploded view of a multi-cartridge variable beam angle fixture 1200. Each of the 3 bulb cartridges or heads 900 ride in ceramic saddles 1218 that have conductive spring clips 1220 that retain the metallic pins 920 and 922 of the bulb cartridges 900 as well as connect power to bulb cartridges 900. The saddles 1218 and corresponding end caps 912 at one end are a different size than the saddle 1218 and end cap 914 at the other end which allows polarizing the ends so that the bulb cartridge 900 can only be inserted one way and the zero voltage potential 902 is always on the front face and the high voltage potential 904 is always on the back side, away from users.

The saddles 1218 also hold detent springs 1216 which mate with detent ridges and groves on the bulb end caps 912 and 914. This allows the bulb cartridges 900 to have several exact angles that they can easily be set to, the spring 1216 holding them 900 in each position but allowing finger pressure to allow it to snap to the next detent position. The front bezel 1222 of the fixture swings away from the base 1202 by means of a latch and hinged connection 1208 between the front bezel 1222 and the rear housing 1202 to expose the bulb cartridges 900 for maintenance or replacement. When the front bezel 1222 is closed completely it presses against a safety switch 1210 which is mounted in the rear housing 1202, the pressed microswitch 1210 then enables power to the fixture 1200. Proximity and distance checking is also determined by distance sensor 1214 which looks through a small hole in the bezel 1222 and checks distance to the closest object or floor. The safety switch 1210, distance sensor 1214 and data from the 3-bulb cartridge's smart chip and thermo sensors 916 are all connect to and coordinated by the smart power supply 1204. The power supply 1204 also has digital communication capabilities such as Wi-Fi and Ethernet to name just a couple. Air is pulled through perforations in the front bezel 1222 by a fan 1206 that is supported by a fan frame 1224 then blows this air over the top of the power supply 1204 and over the bulb cartridge's heatsinks 910 and out through holes in the base 1202. The power supply 1204 measures bulb cartridge 900 temperatures and modifies the fan 1206 speed for optimum efficiency of the bulb cartridge 900 efficiency. A mounting plate 1226 is capable of mounting first to standard electrical boxes found in existing architectural situations and then the plate snaps to the rear housing and can spin in the rear housing tracks to allow the upper bezel to aim in infinite directions. Because UV C light filters tend to allow light to only pass at narrow angles the emitted light tends to be in a narrow beam. This inventive fixture allows for multiple heads in a single fixture to allow for wider beams and asymmetrical light dispersion to best fit the widest range of environmental confines. Ideally the fixture would have an illuminated indicator 1228 to show functions and or faults from a distance, in the illustration the indicator 1228 is a backlit logo. The preferred embodiment shows 3 bulbs in a fixture but any number of bulbs could be used in the inventive device. The advantage of having more than one bulb emission angle allows for better isotropic performance. That means more sources of light coming from different angles kills pathogens better in a dynamic environment than a single narrow beam of the same total power, even if the inventive multiple light system 1200 could not swivel, even if the lights were a tight beam and not diffused, it would be superior to a single bulb angle system.

Figure 13:
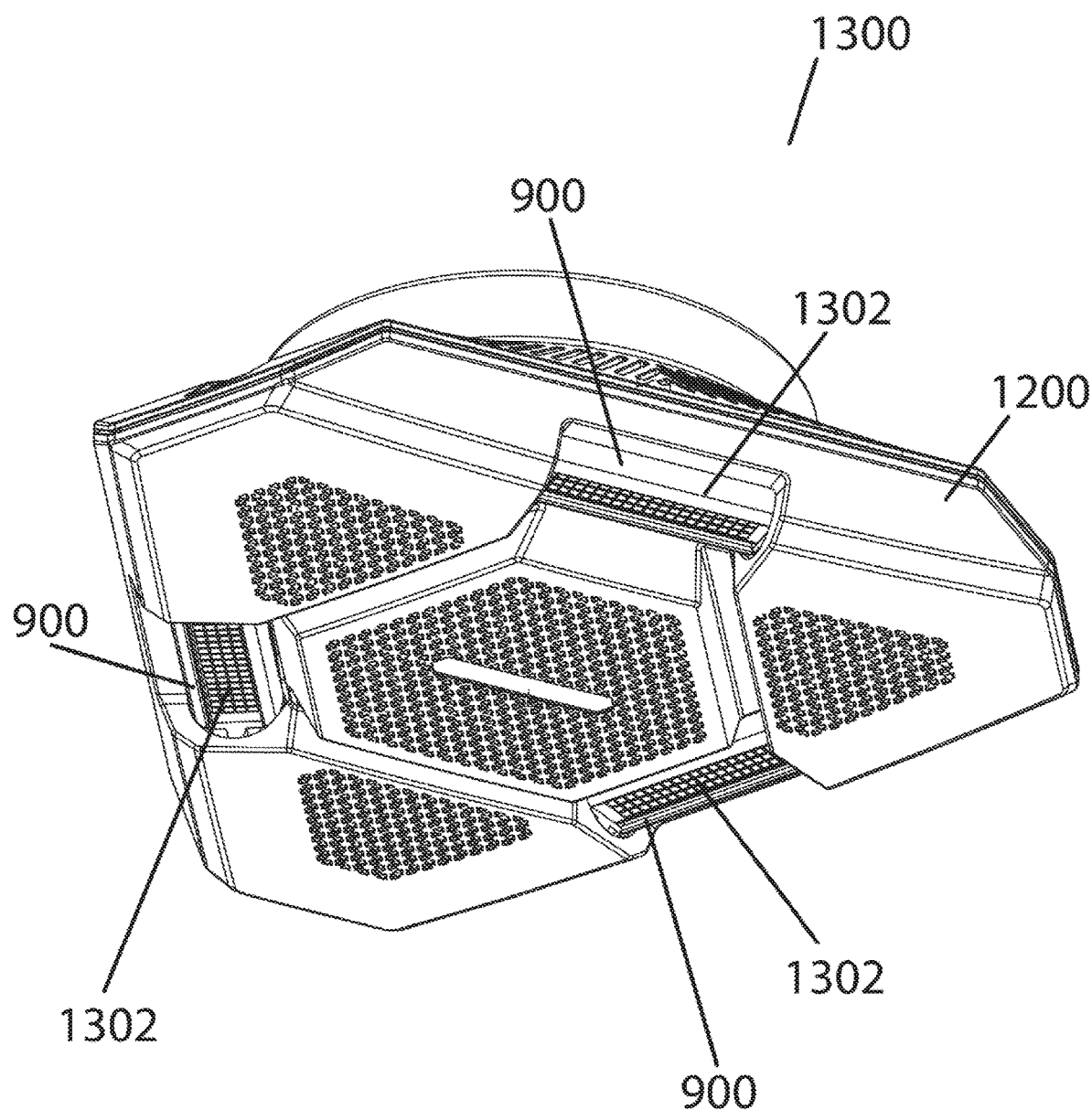
FIG. 13 Depiction of fixture aiming down with bulbs aiming straight down.

In FIG. 13 Depiction of fixture aiming down with bulbs positioned straight down 1300. Fixture 1200 has 3 bulb cartridges 900 aimed straight down 1302 for a tight beam angle under the fixture 1200. This forms the narrowest beam possible for the fixture and would be used in situations where there is a very high ceiling or where the emitted light needed to be concentrated.

Figure 14:
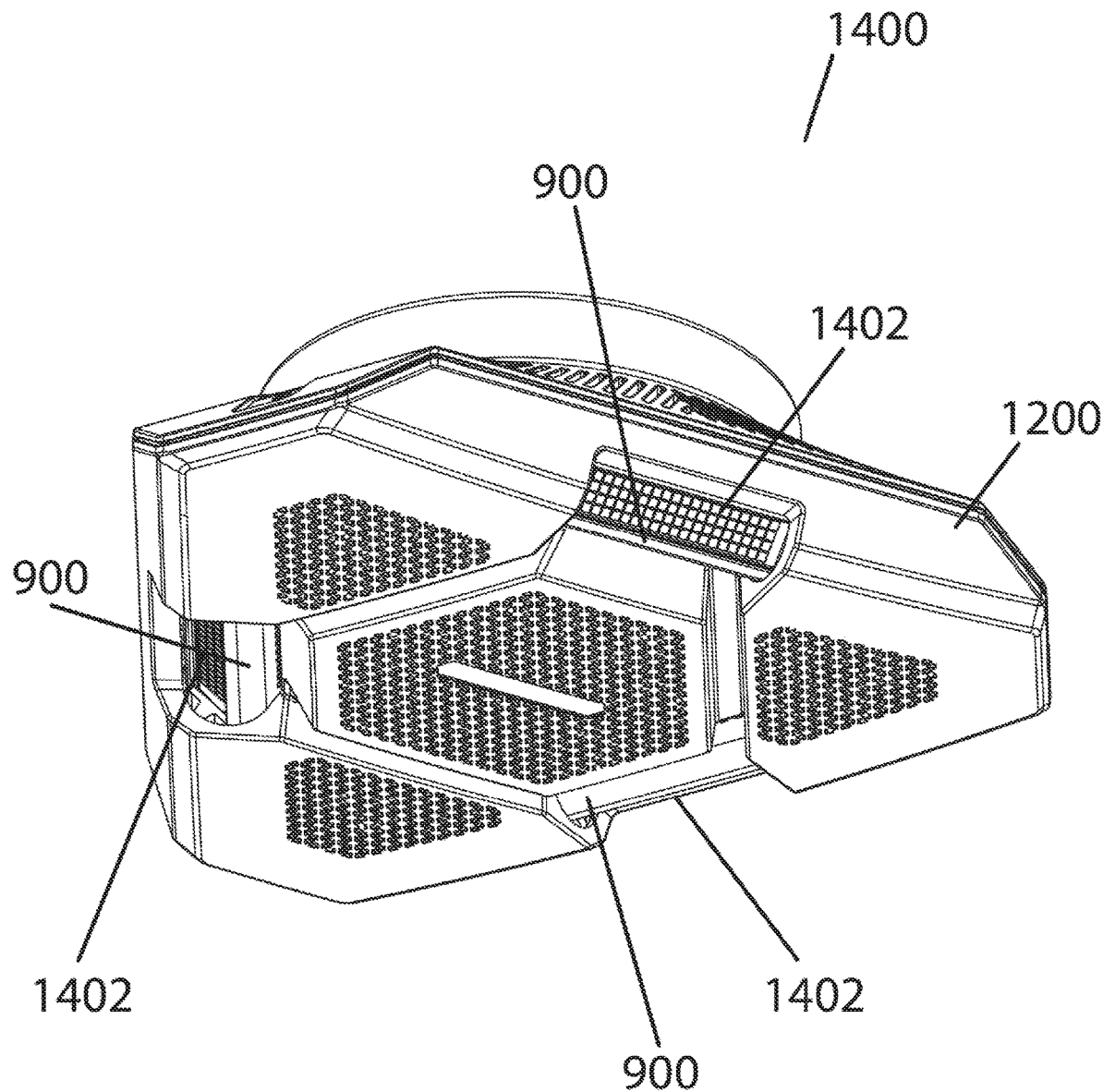
FIG. 14 Depiction of fixture aiming down with bulbs aiming out at 45 degrees.

In FIG. 14 Depiction of fixture aiming down with bulbs positioned at 45 degrees 1400 where fixture 1200 has 3 bulb cartridges 900 aimed out at 45 degrees each 1402. The wide beam angle under the fixture 1200 and would be used on lower ceilings or in areas with a very wide area to be covered.

Figure 15:
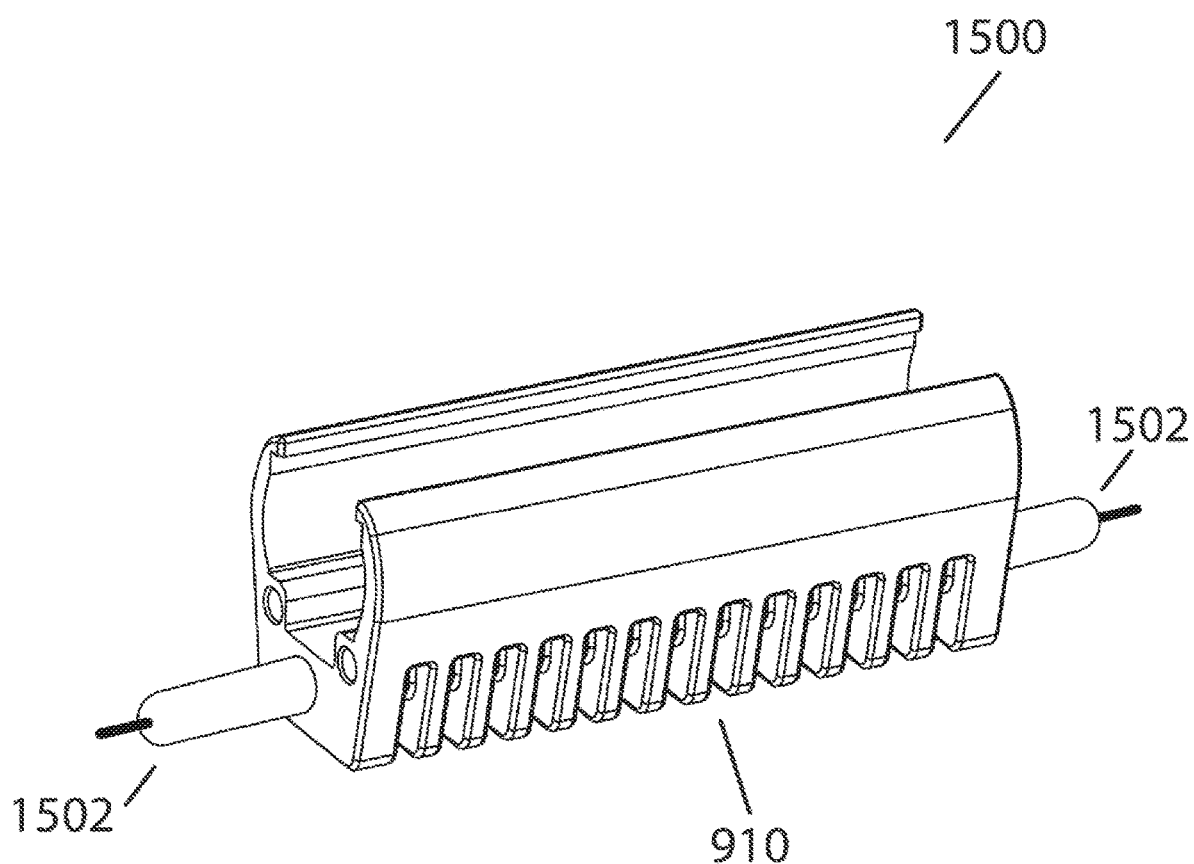
FIG. 15 Safe bulb heat sink with heating filament.

In FIG. 15 Depicts a safe bulb heat sink with a heating filament 1500. The heatsink 910 can be modified to have a heating element 1502 that is permanently installed through a hole in the heatsink or is simply embedded in the ceramic along its long axis. This heated heatsink 1500 will conduct heat to the bulb 800 and warm the gases inside making them able to ignite when requested. Electrical heating elements

1502 are over 100 years one hundred years old and well understood by one skilled in the art. This heating element 1502 is controlled by the smart power supply 1204 when needed to start the fixture 1200 during cold conditions. Once the bulbs 900 are operating they warm up and the heating element 1502 can be turned off. Extra electrical contacts would be required for this inventive addition to the excimer bulb assembly.

Figure 16:
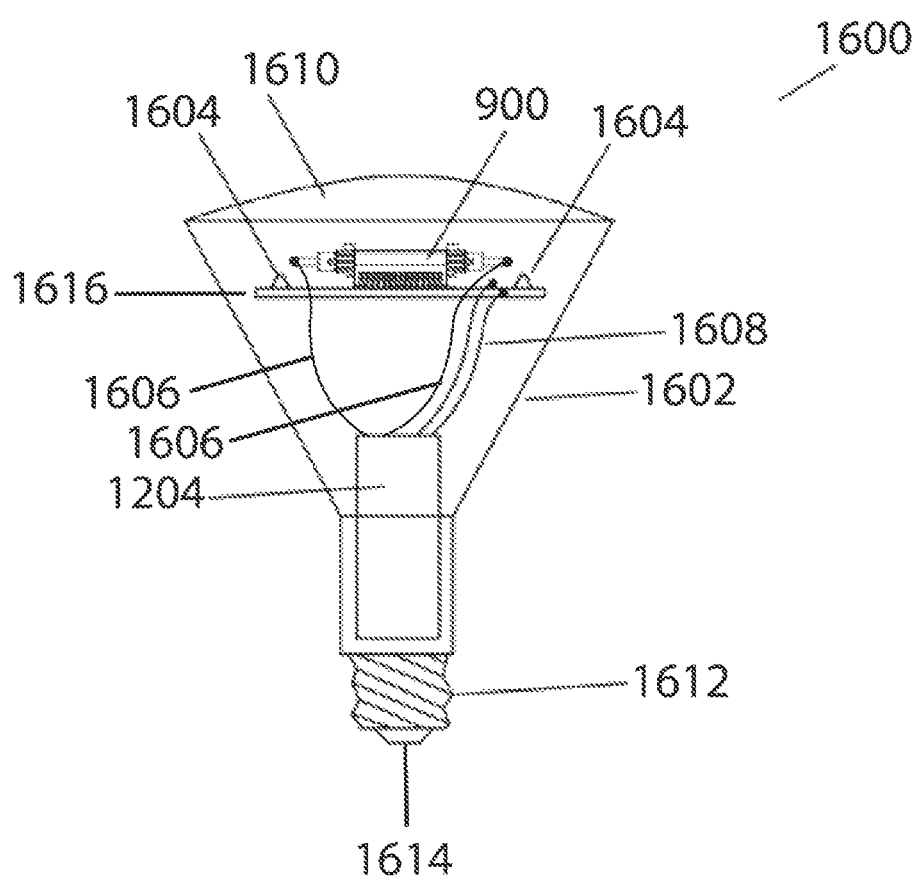
FIG. 16 Safe Bulb with both UV-C and general illumination elements.

FIG. 16 depicts a side view of a screw-in UV-C safe bulb 1600. For means of illustration only this depiction uses a flood light type bulb 1602 but any type of screw in bulb would be applicable regarding this disclosure and this disclosure is not meant as a limitation in any way, just one example. The safe bulb with both UV-C and general illumination elements 1600 is placed inside a screw-in bulb housing 1602. The traditional electrical contacts of said screw-in bulb 1612 and 1614 go to the driver/power supply 1204. The driver/power supply 1204 then powers the UV-C portion 900 of the safe bulb with both UV-C and general illumination elements 1604 through wires 1606 on circuit board 1616 the wires go to clips mounted on the circuit board, the clips were not shown for simplicity. The driver/power supply 1204 also powers separately the white LED 1604 portion via wires 1608. The translucent face 1610 of screw-in UV-C safe bulb 1600 needs to be made of quartz glass, ideally with a diffused surface such as sandblasting or other texture. UV-C would be absorbed by any plastic or traditional glass cover. The inventive flattened cylinder bulb 900 is combined on a circuit board 1616 with a number of LEDs 1604. The LEDs could all be one color of white or they could be a mix of colors or different color temperatures with individual LED 1604 control to mix LEDs 1604 of different colors. The color of light emitted by just the safe UV-C portion of this inventive device will not be optically bright to the human eye, and it will also include a pinkish purple cast. The white LEDs could be pink or purple deficient so that when both the safe UV-C and white LEDs are turned on, the combined light would have a neutral color spectrum.

Figure 17:
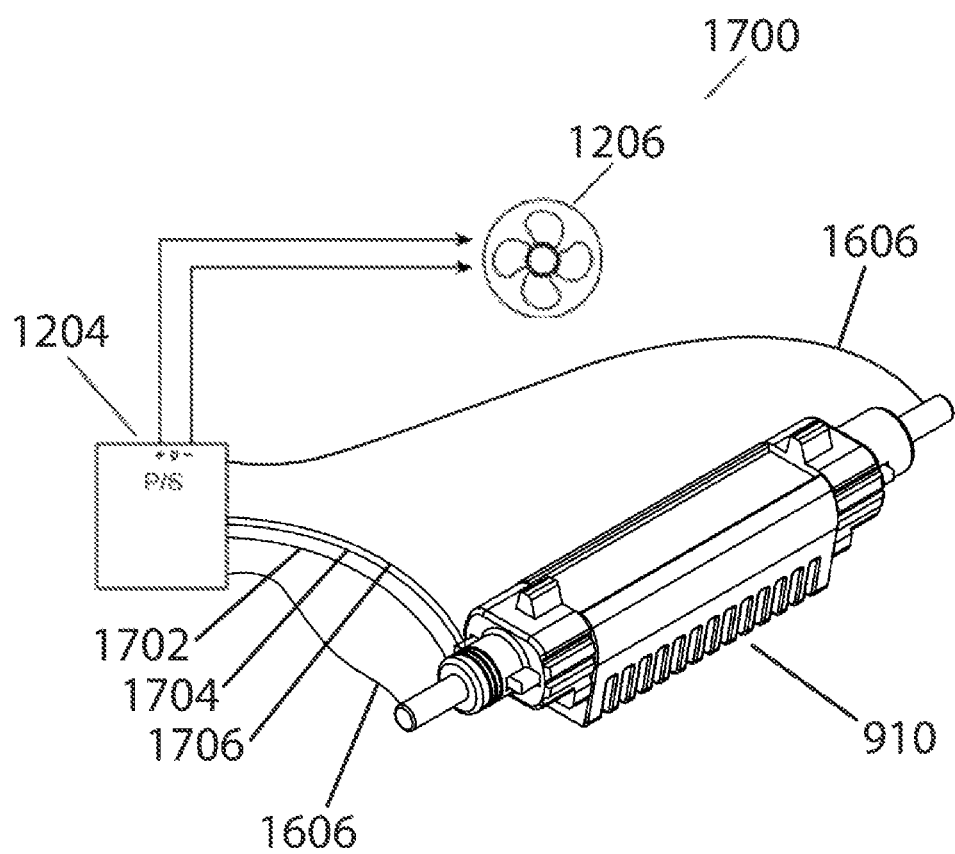
FIG. 17 Temperature regulated fixture with fan-cooled safe bulb.

FIG. 17 depicts fixture with a temperature regulated fan-cooled flattened cylinder safe UV-C bulb fixture 1700. The smart power supply 1204 is in communication with the smart chip 916 in the bulb 900 through the low voltage data lines. Above the heatsink 910 is a small muffin fan 1206 that blows down on the heatsink 910 and bulb 900. The fan is controlled and powered by driver/power supply 1204. The thermal sensor 916 encased inside the ceramic base is interrogated by the smart driver/power supply 1204. Based on the power being sent to the bulb 900 and the reported temperature the driver/power supply 1204 will drive the fan 1206 to an appropriate speed in order to regulate the temperature of the bulb 900 in a closed loop. The heatsink 910 may or may not be necessary because lower powered bulbs would not need the heat sink 910, higher powered bulbs might need a big heatsink or a pin-fin heatsink 910, by example and not by limitation. The driver/power supply 1204 will also power resistive heaters when the bulb 900 has not been on and the thermal sensor detects that bulb ignition might not be possible due to low temperatures. The driver/power supply 1204 would then power the resistive heater before applying power to the bulb 900. Later once the bulb 900 was operating the driver/power supply 1204 might have to power the fan 1206 to cool down the bulb 900. The power supply powers the excimer bulb using pulse wave high voltage DC power in the inventive fixture. The width of the individual pulse waves can be altered to control brightness of the bulb 900 or some of the pulse waves can simply be skipped to dim the light's output. Most excimer bulbs are presently driven by sine wave power supplies and they have too much un-harvestable energy below 9,000 volts. This energy simply heats the envelope and doesn't generate light. The pulse wave may have a bit of a rounded top but otherwise looks like a square wave, it has straight sides, no unusable power. The bulb's predicted output over time can be programmed into the power supply so that as the hour meter in the bulbs age and report, the power supply could raise the power slightly to compensate for the lower efficiency to have a constant lumen output over time.

Figure 18:
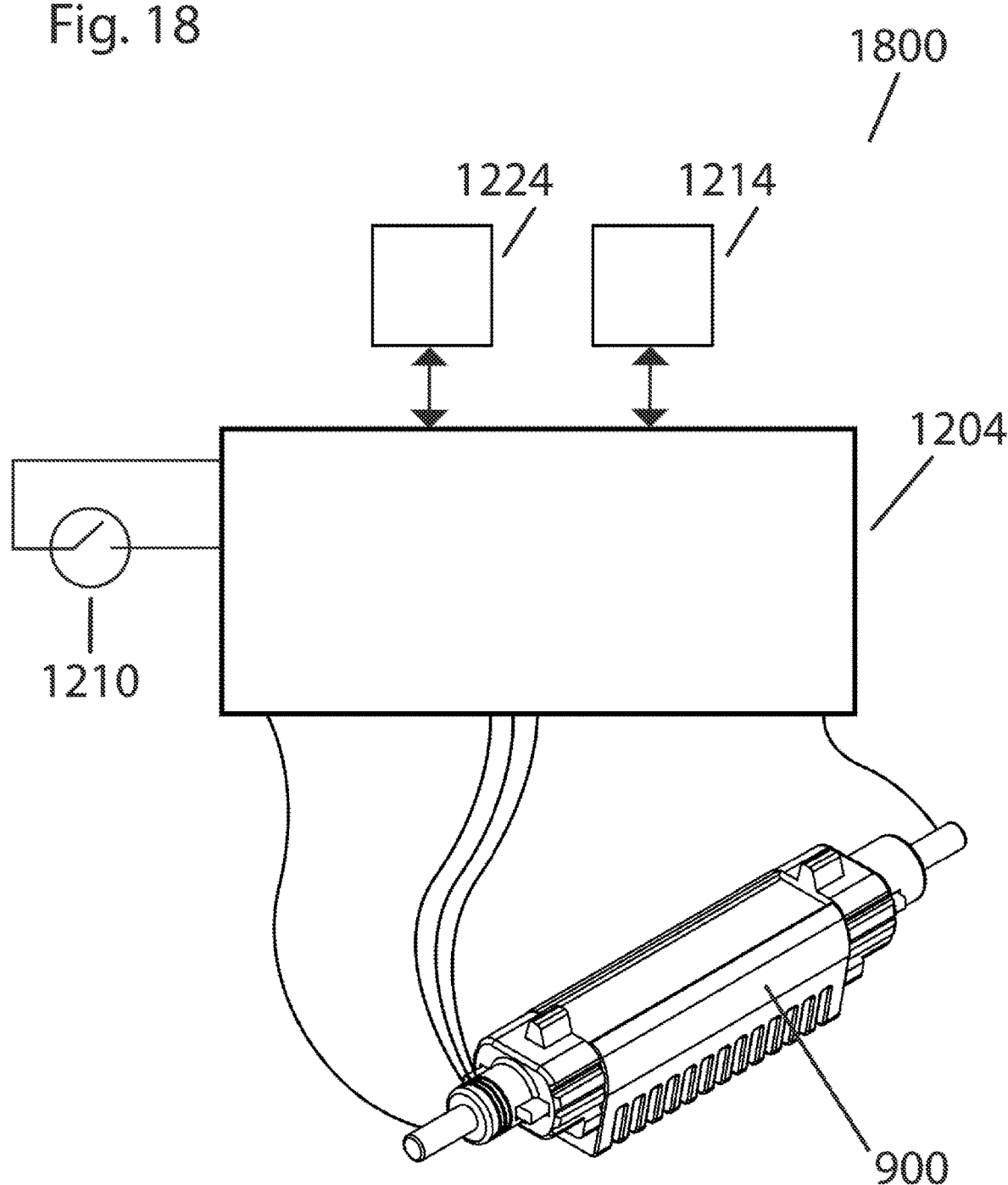
FIG. 18 Block diagram of a fixture including driver, bulb, temperature sensor, and safety cutoff switch in a fixture.

FIG. 18 is a block diagram of driver, bulb 900, distance and proximity sensor 1214, light level sensor 1224, smart chip 916 and safety cutoff switch 1210 in a fixture enclosure. The bulb 900 is connected to the driver/power supply 1204. The driver/power supply 1204 has a switch 1210 wired to the door or front bezel 1222 of the fixture enclosure so that whenever the door 1222 is open, power to the bulb 900 is turned off. This is an especially important safety issue because excimer lights can operate using several thousand volts. The driver/power supply 1204 talks to the smart chip 916 and verifies that this bulb 900 is valid and has not been tinkered with and is a valid replacement via communication with the smart chip. Counterfeit bulbs would most likely not have the pass-filter and would emit dangerous wavelengths towards the user. The distance/proximity sensor 1214 makes sure that the output power level is appropriate for the distance to the ground and could change the output power lever to the bulbs based on the distance. The proximity sensor 1214 and smart power supply 1204 look to lower power levels or turn off if it detects objects at very close distances such as a maintenance person trying to work on the fixture 1200. The proximity sensor and distance sensor 1214 could be the same sensor. The UVC light level intensity sensor 1224 could either look at the ground or at the bulb. It would be filtered to only see 200 nm-230 nm wavelengths. It could determine total light output and the smart power supply/driver could use this information to adjust the output for constant lumen output. Smart functions of the power supply 1204 could be moved to a sperate circuit board and that board could then control the power supply 1204. Such functions are well known by one skilled in the art.

Figure 19:
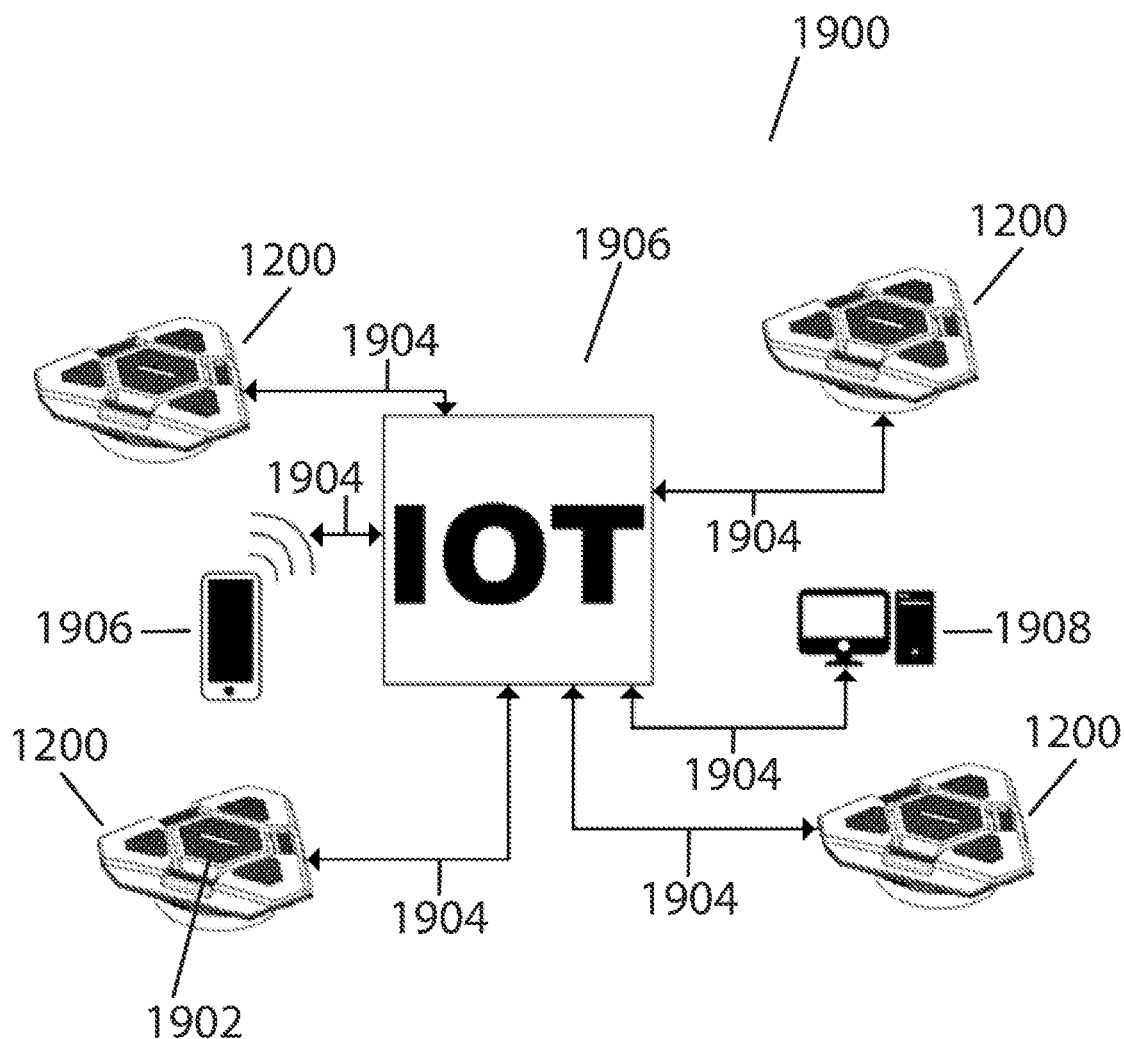
FIG. 19 Network diagram of IoT bulb and system.

FIG. 19 Is a network diagram of IoT bulb and system 1900. The inventive device 1200 may have LEDs 1228 on the basic light fixture 1200 that will indicate that it is on and disinfecting. This could be a constant LED 1228 or intermittent LED 1228. Similar to a smoke detector, the light 1200 will be "good" or "OK" in one color IE Blue or Green when functioning properly and will turn to "attention" or "error" in another color IE Amber or Red. The indicator 1228 could be in the form of a backlit logo.

People entering a room can quickly look and see that the light 1200 is functioning or needs maintenance by looking at the LED 1228. The led 1228 may also indicate output level. When there is low activity and low bacterial load events it could have one LED on, when there is high activity with increased bacterial load events, the light increases output and the LEDs 1228 will change to signal this event. The fixture could receive data from crowd density sensors and use this information to set the output power levels.

Crowd density sensors 1906 such as CrowdScan 1906 an rf monitor from Antwerp or Density 1906 which is a Lidar based device from San Francisco have the ability to determine how many people are in a given space at a given time without violating their privacy, i.e. using cameras or cell phone snooping techniques. There are several more services similar to these which are simply examples of crowd density sensors 1906 that communicate as IoT 1906 and internet resources such as the inventive device 1900.

The light 1200 may integrate several different kinds of communication 1904 to include BlueTooth 1904, WiFi 1904, Cellular 1904, Sidewalk 1904 from Google, and hard-wired technologies 1904 to mention a few. This communication 1904 will allow for the monitoring of the light function and allow remote control of the light by remote means.

The light 1200 may have local mechanical control systems such as simple on/off and dimmable light switches. The light(s) 1200 may also have a control panel with switches and LEDs to control many lights. The LEDs in the panels can show status or light (on, off, status, etc.). The inventive device lights 1200 can be integrated with other traditional visible/functional lighting. These physical controls would allow controls over those lights also. Physical controls can vary depending on the light fixture application. For applications the fixture 1200 is installed permanently in a space the controls can be integrated into the facility infrastructure. For stand-alone portable applications the controls may be fully integrated into a light 1200 to include integrated power source with power level indicators and a graphic user interface display and control panel.

The light fixture 1200 can communicate 1904 to facility/installation managers and operators. The information can be accessed by a smartphone application 1906, web interface on a laptop 1908 or desktop 1908. The fixture 1200 will push information to the site and the operator can pull information from the light 1200. The wireless interface can be customized for different users' needs. The light 1200 can communicate what output level it is at, what the energy consumption level is, internal temperature, lifecycle/hours the bulb 900 has been in use and how long till it will need to be replaced, work in combination with motion detection to determine if there is a high bacterial load in the space it is set up in. The operator can also control the level of the light 1200 output and schedule the operation profile customizable to best sterilize the area and optimize energy consumption.

The light fixture 1200 can communicate the status to the public or space occupants. The information can be accessed by a smartphone 1906 application, web interface on a laptop 1908 or desktop 1908. This will reassure occupants that the space is being sterilized. The information can also be displayed on an information display in the space.

Figure 20:
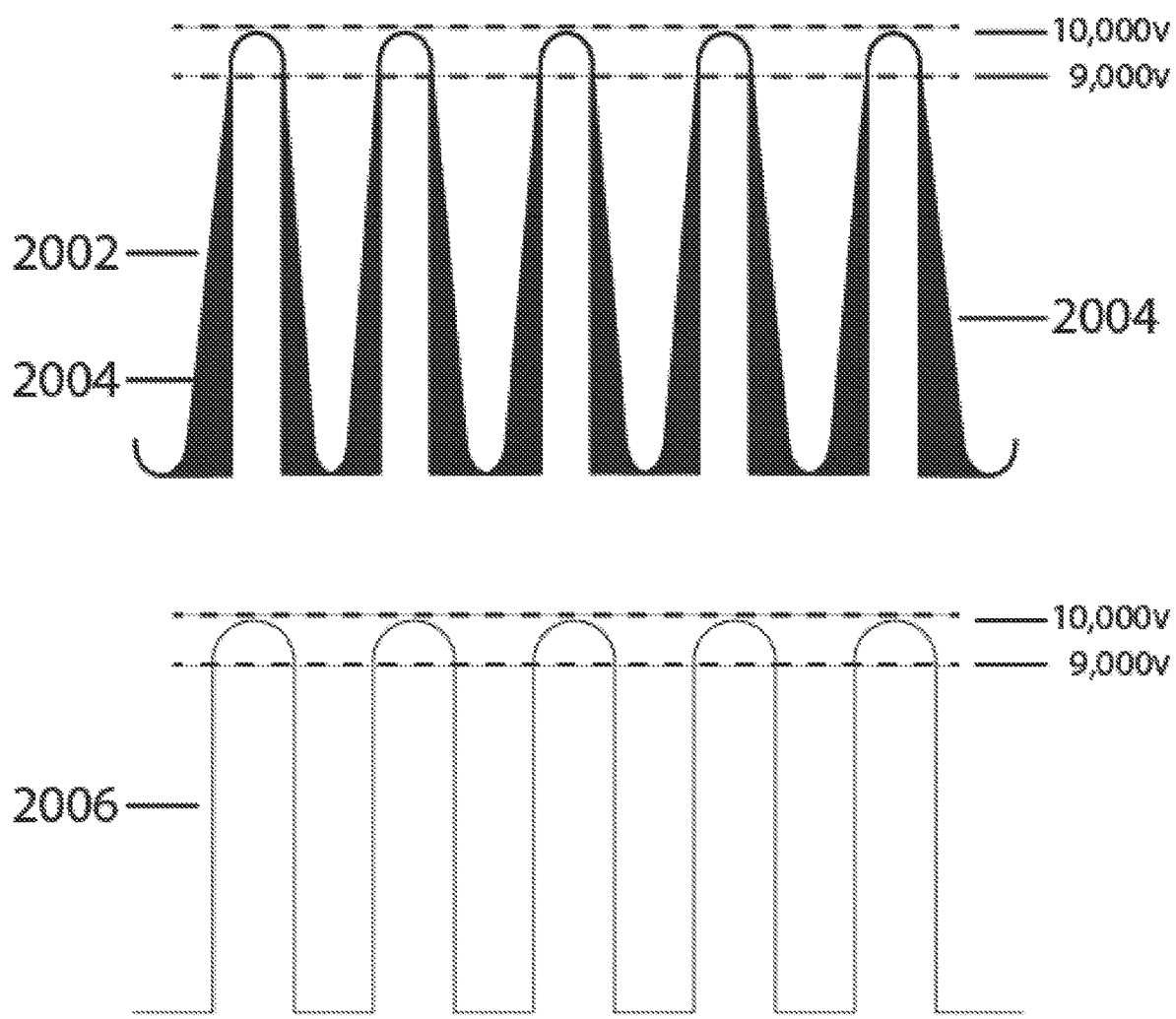
FIG. 20 Depiction of the output of a pulse wave power supply compared to a sine wave.

FIG. 20 is a diagram showing a couple of the power pulse trains used for driving excimer bulbs and showing the differences between 10,000 volt sine wave 2002 power compared to 10,000 volt pulse wave 2006 power. Only the top voltages between 9,000 and 10,000 volts which are shown in the light areas make usable light. All voltages below 9,000 volts simply make heat and that heat minimizes the power level that a bulb can be driven to. The dark area 2004 between the outline of the sine waves and the center white areas are all wasted power and turns to heat that is generated inside the bulb that does not come out as light. Heat causes the breakdown of chlorine gas and that dictates a shorter lifetime of the bulb. There is no wasted voltage in the pulse wave power supply example. The inventive device 1200 would ideally use pulse wave power 2006 in its power supply 1204. This should provide a 50-100% increase in bulb efficiency over the existing sine wave based UV C fixtures. It is also possible to lower the voltage of the pulse wave 2006 below 10,000 volts to dim the bulb's 800 output. The voltage range based on the supplied graph would be 100% at 10,000V and 0% at 9,000V, which is a very narrow voltage range that has to be modified and controlled.

Figure 21:
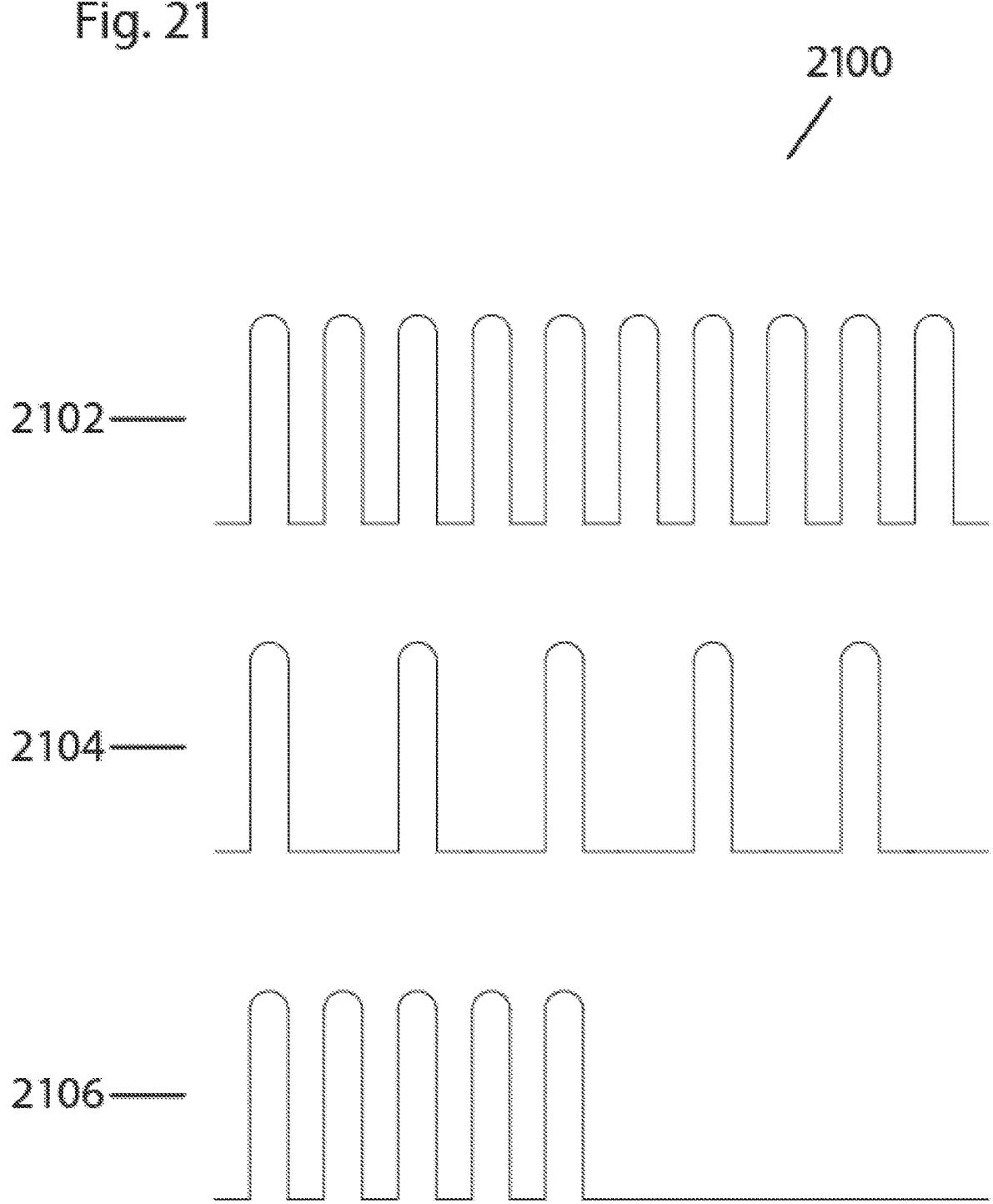
FIG. 21 Depiction of the output of a pulse wave power supply at full power and during dimming.

FIG. 21 is a diagram showing the power pulse train 2100 for driving excimer bulbs where the pulse wave 2102 is at 100% and a pulse wave 2104 at 50% dimming using a symmetrical pattern by reducing every other wave, and a pulse wave 2406 at 50% dimming using an asymmetrical pattern. The power supply simply has to remove individual pulses to reduce brightness and because the pulses are so fast, between 10 k Hertz and 250 k Hertz small dropouts are not obvious and the amount of visible light generated is negligible even at 100%. The smart power supply has a microprocessor that subtracts some of these pulses to dim the fixture's output to any level down to 1% or lower. This technique is well understood to those skilled in the art. These graphs are for examples only, the actual voltages will vary with bulb design and internal gas compositions.

Figure 22:
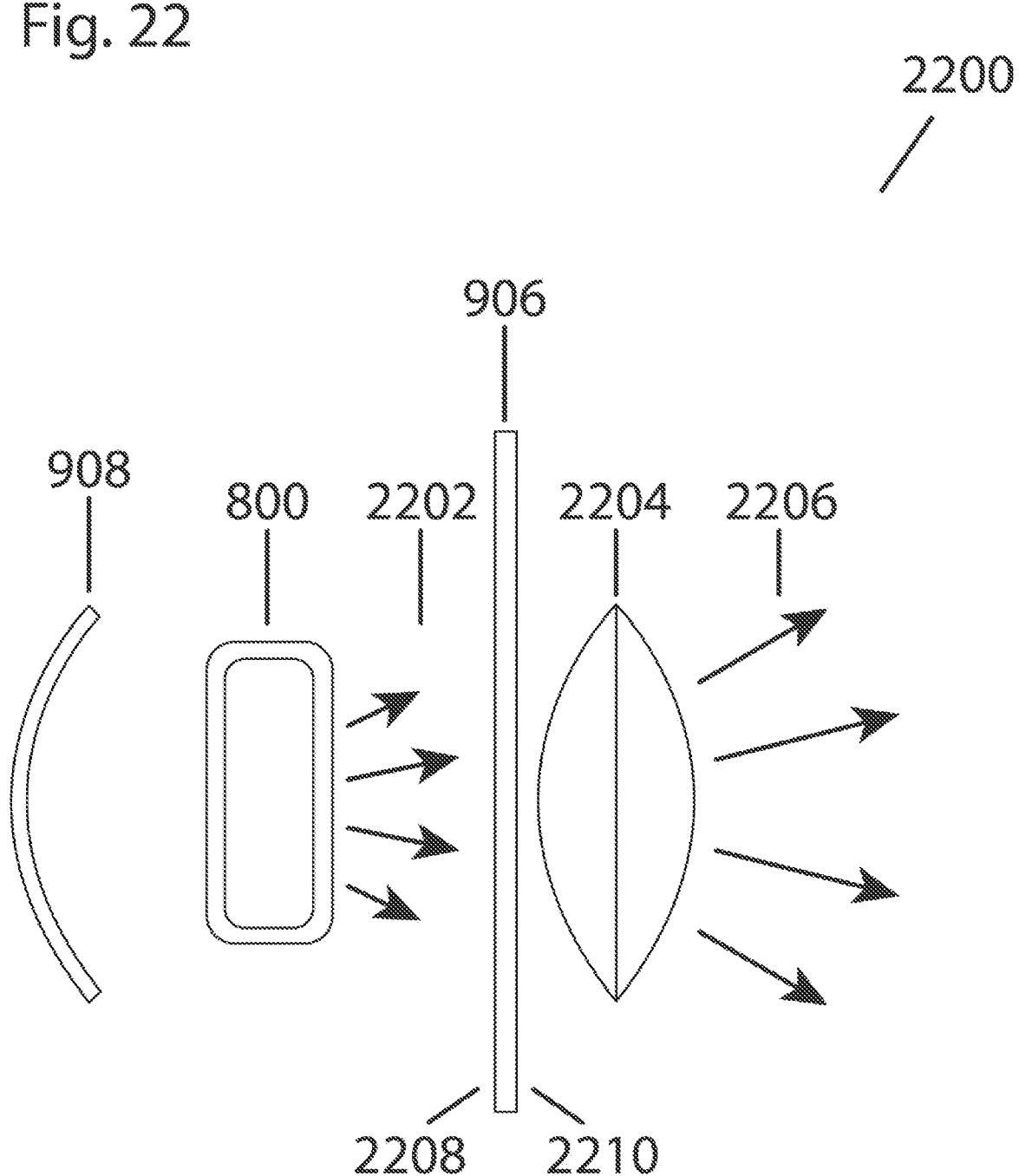
FIG. 22 Depiction of a focusable UVC light for wider beam angles.

FIG. 22 Shows a side view depicting an excimer bulb 800 with variable focus as a system 2200. The bulb 800 has positioned in the light path 2202 a quartz lens 2204 with light shaping capability. The lens 2204 can be round and symmetrical or linear to best match the initial optical path 2202. The lens 2204 could also be continuous or a Fresnel which is stepped. The lens 2204 can be moved closer or further to the excimer bulb 800 to change the focus and spread or narrow the beam angle of the finally emitted light 2206. A variable focus system could also include a reflector 908 which would ideally be curved and it could be moved closer or further from the bulb 800 to change the angle of light emitted from the system 2200. Additionally because the filter 2208 tends to make a narrow beam of light, the lens 2204 could be replaced or supplemented with a diffusion material 2210 on the outside of the quartz filter glass. This diffusion 2210 could be embossed patterns in the glass 906, glass balls, nano particles, or any material that would spread the light without too much subtractive loss.

Figure 23:
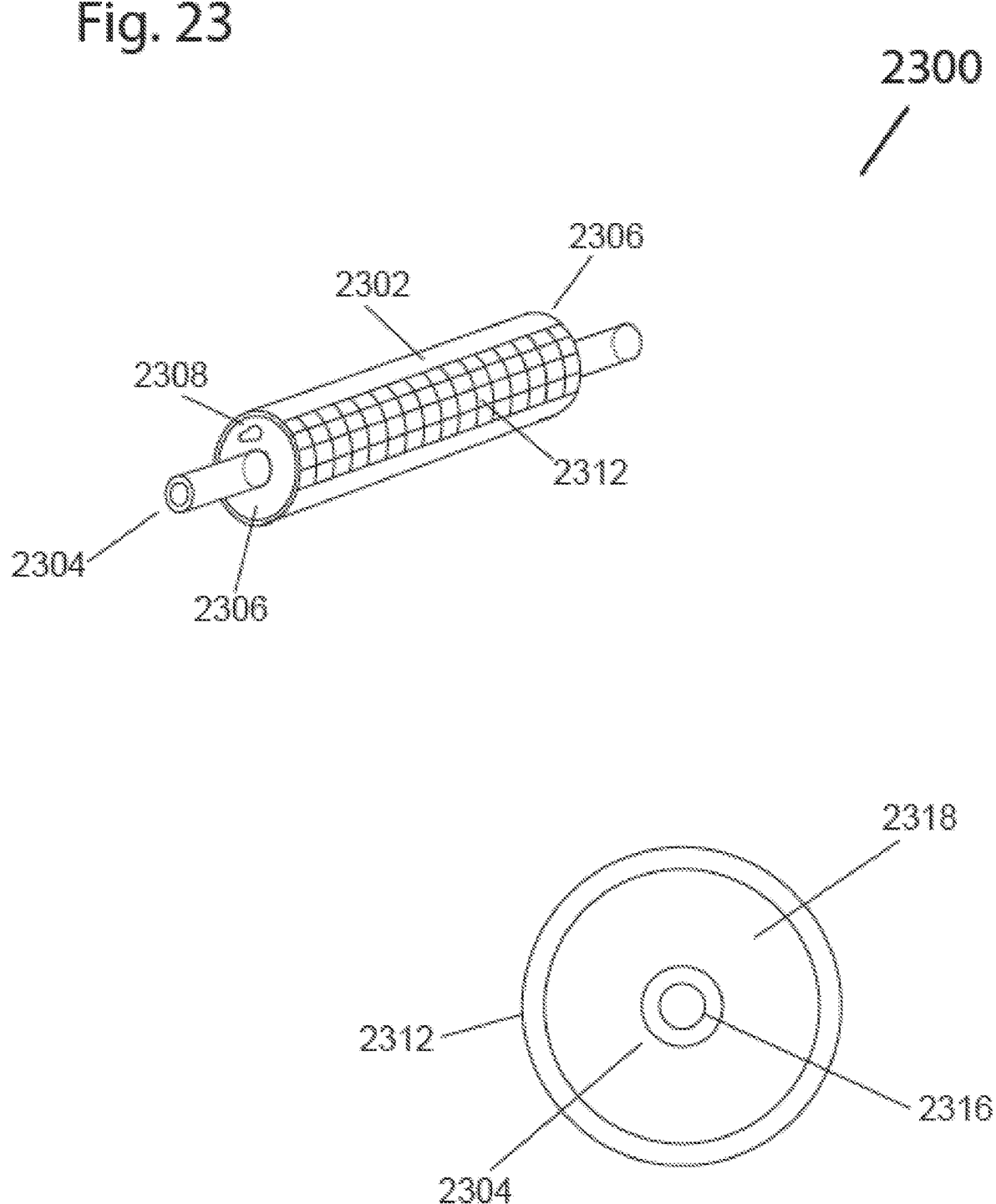
FIG. 23 Depiction of a single-phase dielectric fluid cooled UV C bulb.

FIG. 23 Shows a liquid cooled high power excimer bulb 2300. It consists of an outer envelope 2302, and an inner envelope 2304, where the outer envelope 2302 is shorter and the inner 2304 is longer and they are connected by 2 end caps 2306 which are welded together by heat. The area between the inner and outer has a fill point 2308 on one of the end caps 2306. The fill point 2308 similar to those on existing excimer bulbs and this form chamber 2318 between the two envelopes is evacuated an filled with the appropriate excimer gasses previously mentioned, through the fill point 2308. The outer wall 2310 of the outer envelope 2304 has a conductive grid 2312 adhered to it and it becomes the negative electrode which goes all of the way around the circumference of the tube 2304. Similarly the inner wall 2314 of the inner tube 2304 has a conductive grid 2316 which goes around its inner circumference and becomes the positive electrode. Light exits equally in all directions from this type of bulb.

Figure 24:
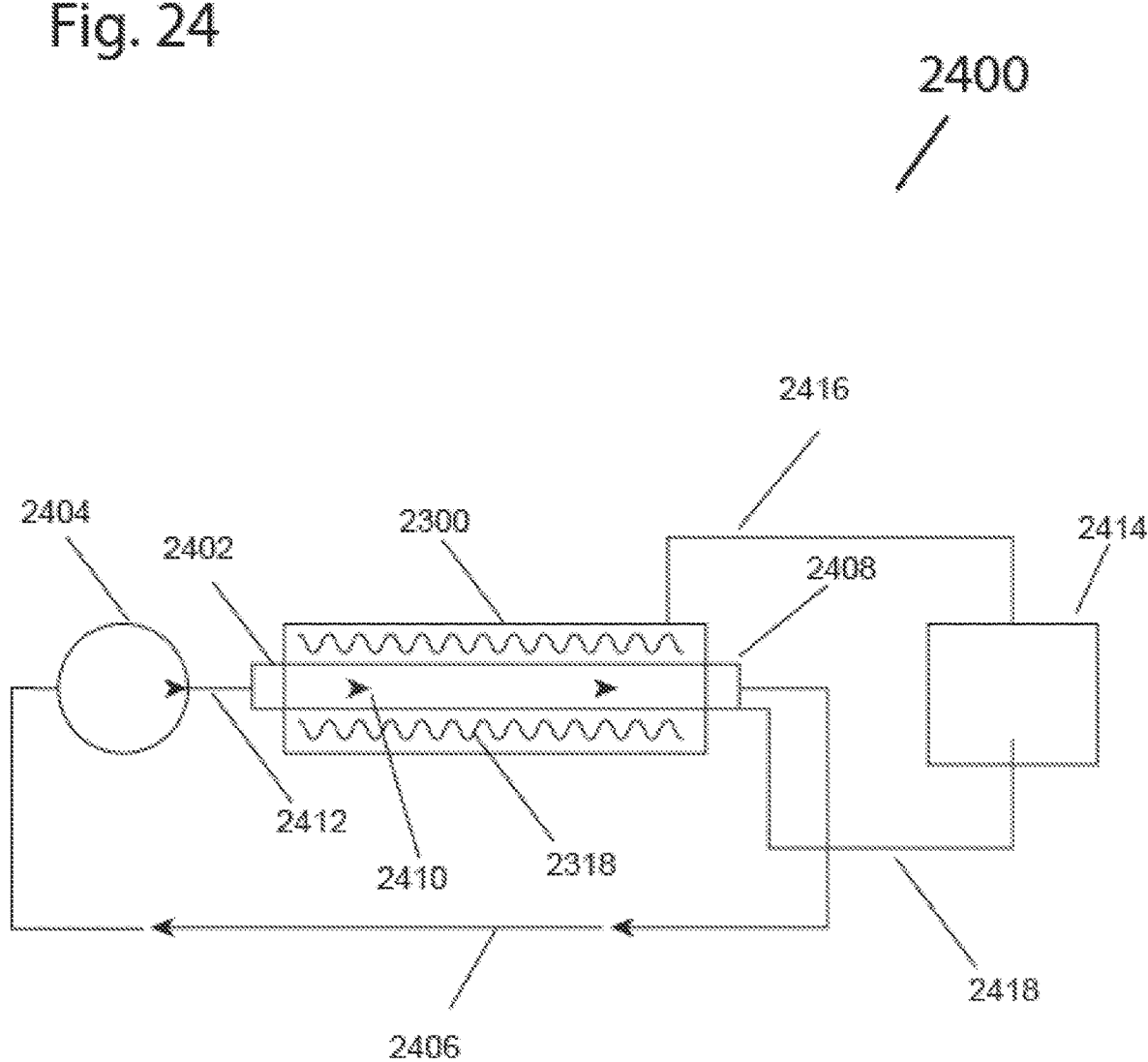
FIG. 24 Depiction of a single-phase dielectric fluid cooled UV C system.

FIG. 24 Shows a block diagram for a liquid cooled bulb 2300 with the coolant system which results in a high powered excimer fixture 2400. The bulb 2300 has a tube 2412 connected to the input end 2402 that connects to a pump's 2404 output. The pump's input is connected to a return loop 2406 of tubing which goes out and around to the output end 2408 of the bulb 2300. Inside of the tubing 2406 and the pump 2404 and the inner wall 2316 is a single phase dielectric liquid which is circulated using the pump 2404. This dielectric liquid 2410 is typically used in large data centers where the entire server is submerged in a vessel to cool the server components. In general, there are two main liquid categori Hydrocarbons (i.e al, synthetic or bio oils) and fluorocarbons (i.e. fully engineered liquids). The liquid 2410 conducts heat very well but is not electrically conductive which is a very important characteristic for the inventive device 2400, the liquid 2410 will be in contact with the 10,000 volt conductive mesh 2316 of the bulb 2300. Heat is generated in the interior 2318 of the bulb 2300 and this heat is carried away by the pump 2404 and it dissipates to the environment during its trip through the return loop 2406 before reentering the pump 2404, where the recirculation continues. The return loop 2406 might include a separate radiator 2406 similar to what is used in the computer cooling industry, this is well known to those skilled in the art. The power supply 2414 is connected to the bulb 2300 using the negative wire 2416 which connects to the exterior mesh 2312. The power supply 2414 also connects to the bulb 2300 using the positive wire 2418 which connects to the inner mesh 2316 and is in contact with the coolant 2410. The cooling 2410 allows for much more power to be introduced to the bulb 2300 allowing for an unmatched and powerful excimer fixture 2400.

Figure 25:
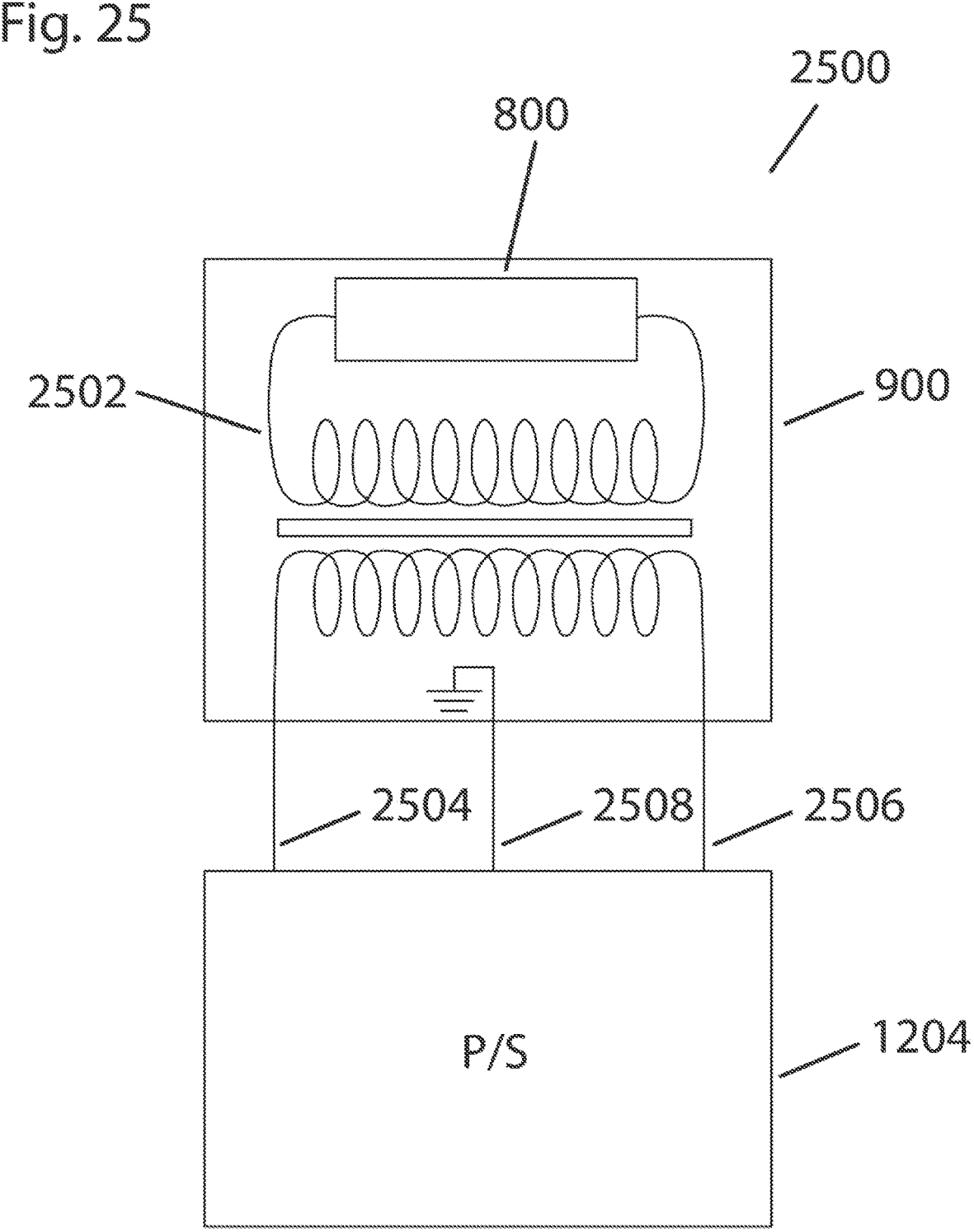
FIG. 25 Depiction of a low voltage UVC bulb system.

FIG. 25 Shows a schematic of a low voltage UVC bulb system 2500. The bulb 800 is driven by a high voltage transformer 2502 which is inside the bulb assembly 900. This allows the bulb cartridge 900 to be closer to surrounding structures because there are no high voltage leads to be routed and separated. This also allows the user to replace bulbs 900 without the risk of shock because the high frequency AC power delivered to the bulb assembly could be 48 VAC. The high voltage transformer 2502 has been separated from the power supply 1204, similar to what is used in flash xenon systems. This could allow for only 2 wires 2504, 2506 to be connected to the bulb assembly, a third connection earth ground 2508 could be optional.

Figure 26:
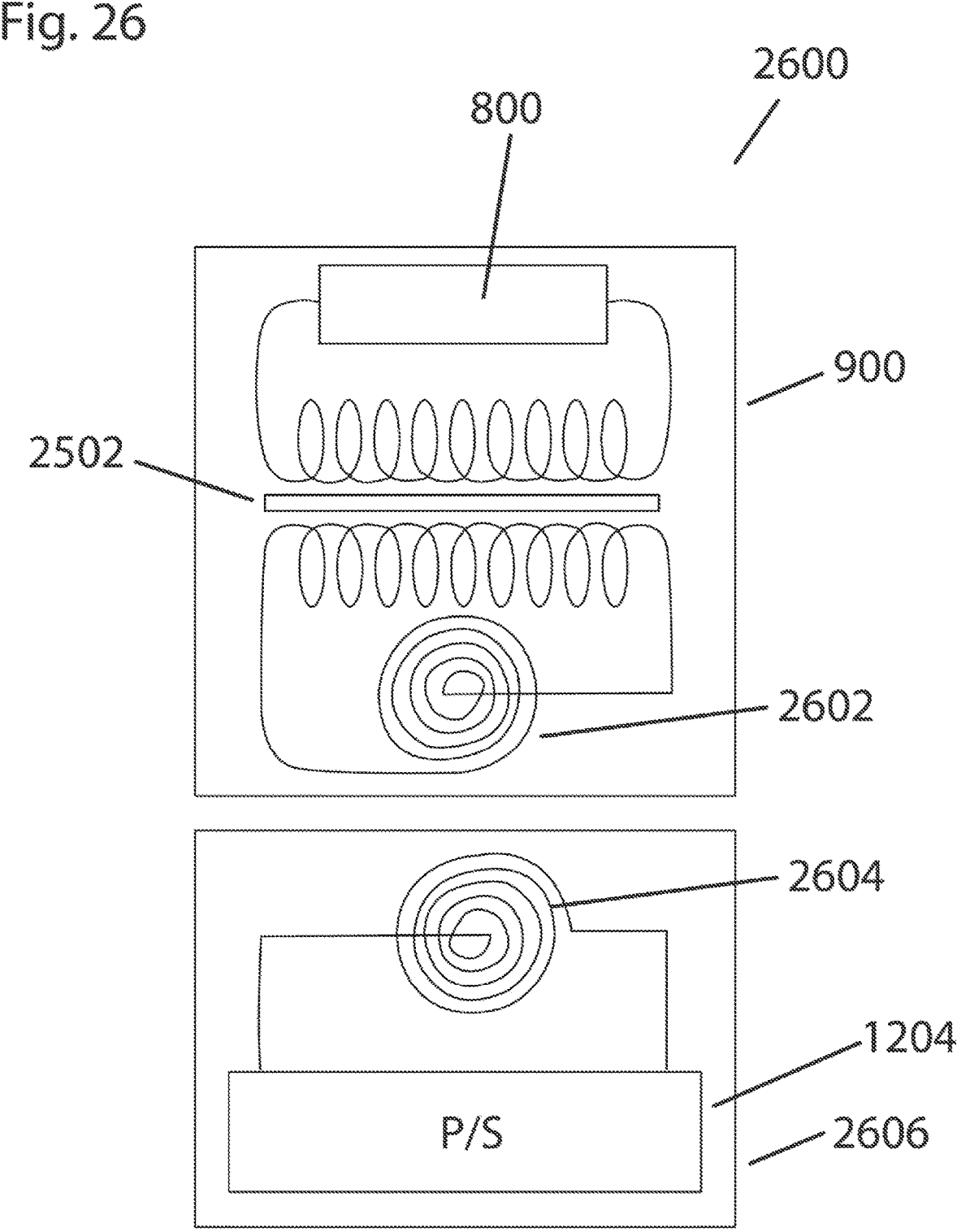
FIG. 26 Depiction of a low voltage inductively powered UV C bulb system.

FIG. 26 Shows a schematic of a low voltage inductively powered UV C bulb system 2600. The bulb 800 is driven by a high voltage transformer 2502 which is inside the bulb assembly that is powered by a pair of inductor coils 2602, 2604. The bulb side inductor 2602 is physically located in the bulb assembly 900. The power supply inductor 2604 is located inside the power supply enclosure 2606. This allows the bulb 900 to be closer to surrounding structures because there are no high voltage leads to be routed and separated. It also removes any direct electrical connections to the bulb assembly 900. The inductor connection 2602, 2604 is similar to existing cordless cellphone charging devices, except the AC voltages used would be at a very high frequency. And because the bulb assembly 900 can be precisely cradled the efficiency of the inductive bridge 2602, 2604 would be much higher than the cell phone example. This would be the safest excimer bulb imaginable, with no mechanical electrical connections.

Figure 27:
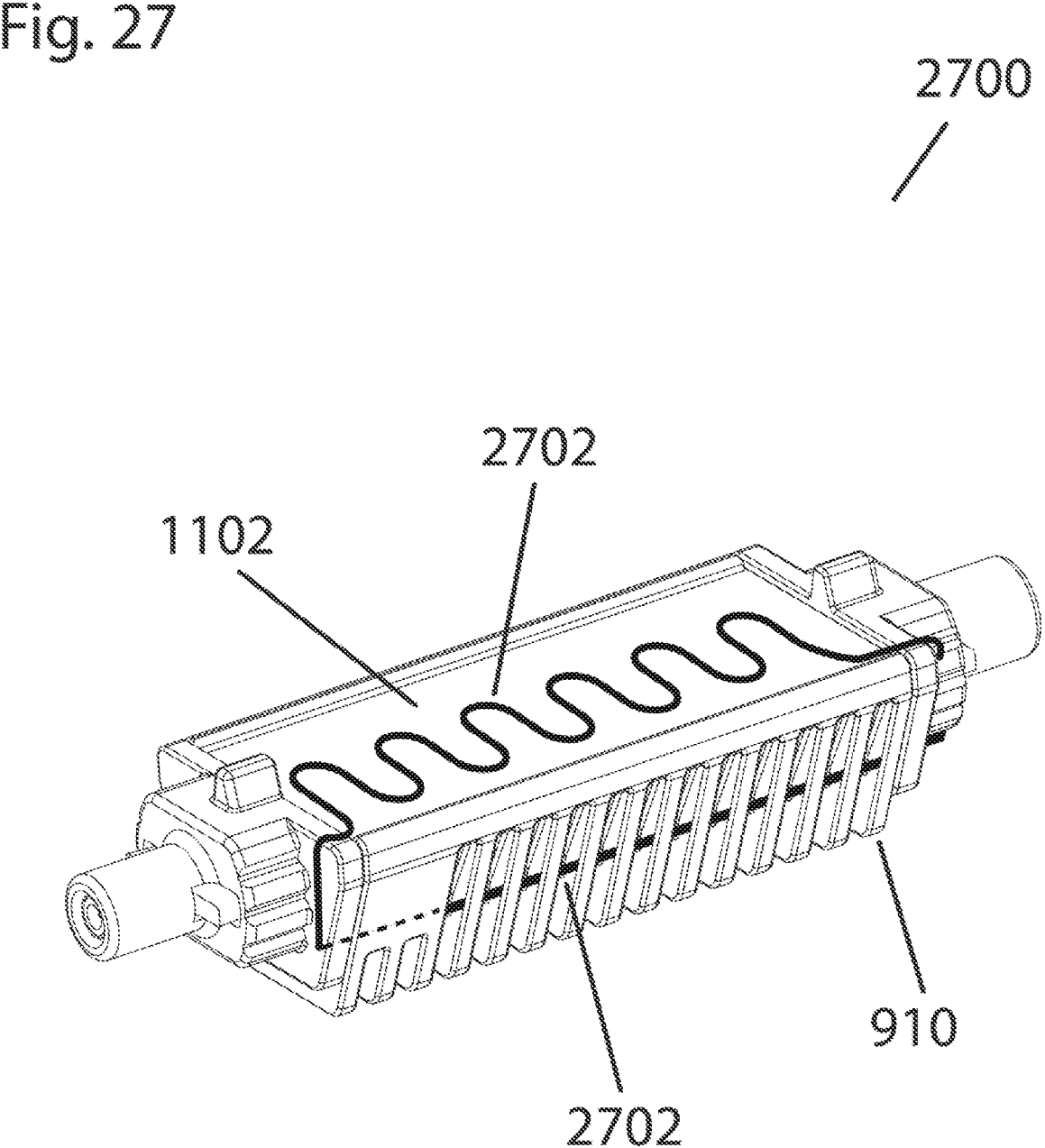
FIG. 27 Isometric view of a safety break wire in a bulb cartridge.

FIG. 27 Shows a isometric view of a protected bulb cartridge 2700 using a traditional bulb assembly 900 with a continuous safety wire 2702. The safety wire runs back and forth across the glass aperture 1102 on the outside and continues through or around the ceramic body 910 of the bulb assembly 900. The wire on the glass could be vacuum deposited aluminum 2702, and the wire on the ceramic housing 910 would ideally be pad printed conductive ink 2702 for ease of manufacturing and cost savings. Compare this drawing to the plain FIG. 11 to best understand the path of the wire. If the wire goes through the ceramic body 910 then it would be placed during the semi-liquid stage of the ceramic fabrication, before firing in a kiln.

Figure 28:
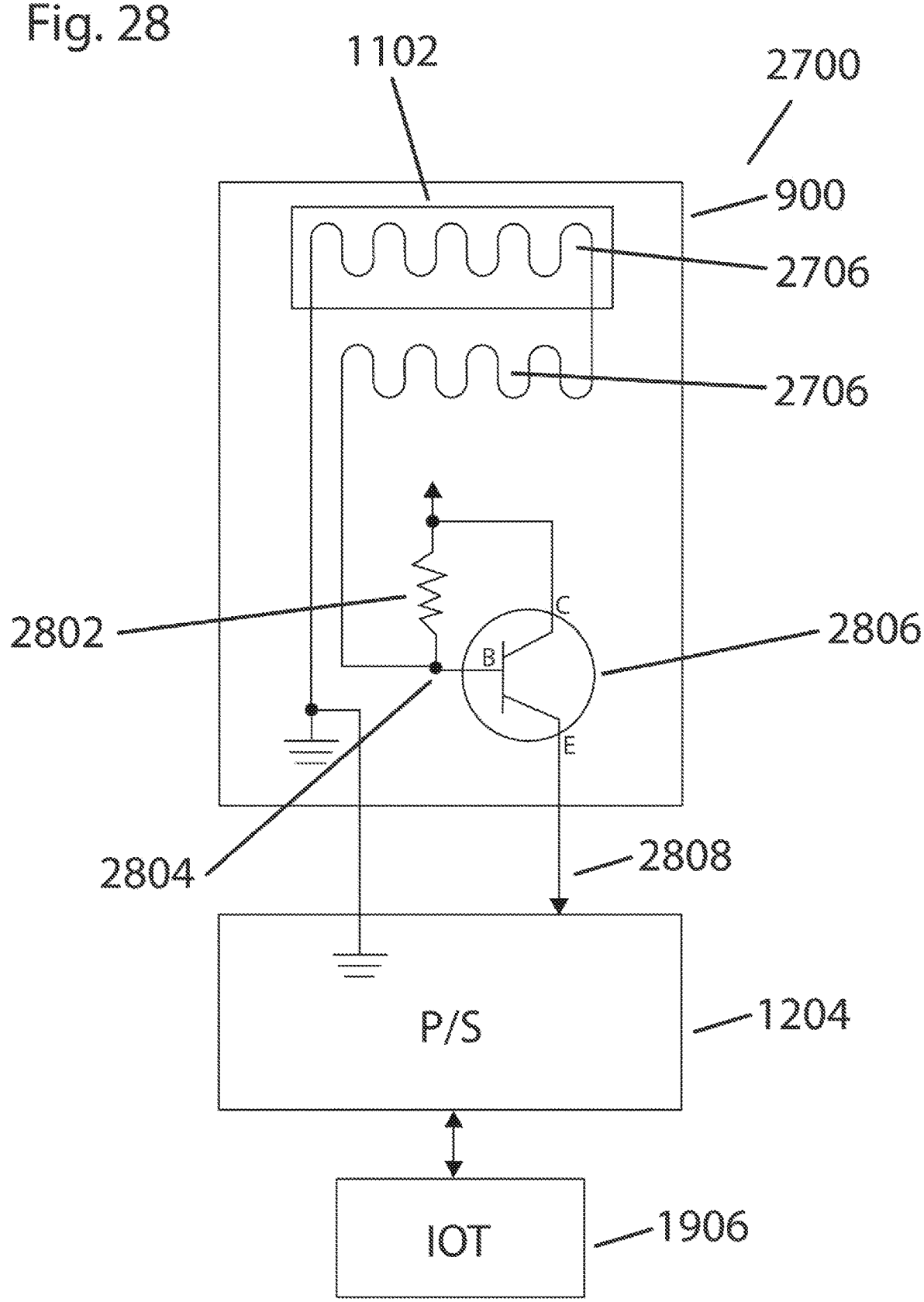
FIG. 28 Depiction of a schematic of a safety break wire system.

FIG. 28 Depicts a schematic of a protected bulb cartridge 2700 system using a traditional bulb 900 with a continuous safety wire 2702. The wire 2702 which could be a trace 2702, much like a conductive path 2702 on a circuit board, begins at one end where it is tied to earth ground and then routed through the ceramic body 910 of the bulb cartridge 900. The wire 2702 continues to run across the glass aperture 1102 of the bulb assembly 900. The wire 2602 then is connected to a small pull up resistor 2702 and the gate 2804 of a PNP transistor 2806. The transistor 2806 is always in the "on" condition if the wire 2702 remains intact, but if the trace 2702 is broken the resistor 2802 pulls the transistor's base or gate 2804 high, this causes the transistor 2806 to turn off, disabling the bulb cartridge 900. The transistor could electrically interrupt the power to the bulb 800 or simply send a signal 2808 to the power supply 1204, much like the safety switch 1210 does in the fixture 1200. The implementation that would use such techniques are well known by one skilled in the art and many other electrical schemes could be used other than the bi-polar transistor that was shown. This would allow fixtures 1200 to be placed to be placed in close and unsupervised proximity to people that could touch and break a bulb 900 but the act of doing so would turn off the fixture 1200. This feature could also be connected to the IOT functions 1906, alerting monitors that breakage had occurred.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The term "at least" followed by a number is used herein to denote the start of a range beginning with that number (which may be a ranger having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Terms of approximation (e.g., "about", "substantially", "approximately", etc.) should be interpreted according to their ordinary and customary meanings as used in the associated art unless indicated otherwise. Absent a specific definition and absent ordinary and customary usage in the associated art, such terms should be interpreted to be ±10% of the base value.

When, in this document, a range is given as "(a first number) to (a second number)" or "(a first number)—(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Thus, the present invention is well adapted to carry out the objects and attain the ends and advantages mentioned above as well as those inherent therein. While presently preferred embodiments have been described for purposes of this disclosure, numerous changes and modifications will be apparent to those skilled in the art. Such changes and modifications are encompassed within the scope and spirit of this invention.

What is claimed is:

1. An excimer bulb assembly, comprising:
   a krypton/chloride excimer bulb and a cutoff filter;
   said krypton/chloride excimer bulb adapted to emit light at wavelengths in the UV C spectrum;
   said cutoff filter including a plane;
   when light emitted from said krypton/chloride excimer bulb at an incident angle of 0 degrees to said plane, said cutoff filter is adapted to substantially block wavelengths longer than 234 nm;
   said cutoff filter allows transmission beyond 237 nm.

2. The excimer bulb assembly of claim 1 wherein said cutoff filter is constructed of a plurality of layers of hafnium oxide.

3. The excimer bulb assembly of claim 2 wherein said cutoff filter is constructed of less than seventy five (75) layers of hafnium oxide.

4. The excimer bulb assembly of claim 1 further including two electrical connectors wherein said excimer bulb, cutoff filter, and said two electrical connectors form a cartridge.

5. The excimer bulb assembly of claim 4 wherein said cartridge is configured for mounting in a fixture and said cartridge includes a main axis and, when said cartridge is mounted in said fixture, said cartridge is adapted to swivel relative to said fixture along said main axis.

6. The excimer bulb assembly of claim 5 wherein said cartridge further includes a smart chip.

7. The excimer bulb assembly of claim 6 wherein said smart chip retains hours of use of said excimer bulb.

8. The excimer bulb assembly of claim 7 wherein said smart chip communicates in an encrypted manner.

9. The excimer bulb assembly of claim 1 wherein said cutoff filter is mechanically integral to said excimer bulb assembly.

10. The excimer bulb assembly of claim 6 wherein said smart chip communicates in an encrypted manner.

11. The excimer bulb assembly of claim 1 wherein said cutoff filter is mechanically integral to said excimer bulb assembly.

12. The excimer bulb assembly of claim 1 including a diffusion layer.

13. The excimer bulb assembly of claim 1 including an illumination element having a white LED.

14. The excimer bulb assembly of claim 1 including a translucent optical element.

15. The excimer bulb assembly of claim 1 including multiple cutoff filters.

* * * * *